(12) United States Patent
Buisson et al.

(10) Patent No.: US 10,227,297 B2
(45) Date of Patent: Mar. 12, 2019

(54) PULVERULENT COMPOSITIONS OF A COMPLEX BETWEEN AN ACID AND A METAL HAVING A HIGH ORGANOSULFUR COMPOUND CONTENT AND METHOD FOR PREPARING SAME

(71) Applicant: INNOV'IA 31, Pontaumur (FR)

(72) Inventors: Pierre Buisson, Lagord (FR); Robert Huet, Paris (FR); Sebastien Fournier, Andilly (FR); Jean-Eudes Vendeville, Perigny (FR)

(73) Assignee: INNOV'IA 3I, Pontaumur (FR)

( * ) Notice: Subject to any disclaimer, the term of this patent is extended or adjusted under 35 U.S.C. 154(b) by 0 days.

(21) Appl. No.: 15/560,004

(22) PCT Filed: Mar. 21, 2016

(86) PCT No.: PCT/FR2016/050620
§ 371 (c)(1),
(2) Date: Sep. 20, 2017

(87) PCT Pub. No.: WO2016/151229
PCT Pub. Date: Sep. 29, 2016

(65) Prior Publication Data
US 2018/0065926 A1 Mar. 8, 2018

(30) Foreign Application Priority Data
Mar. 20, 2015 (FR) .................... 15 52336

(51) Int. Cl.
*C07F 19/00* (2006.01)
*G01N 23/20* (2018.01)
*C07C 229/06* (2006.01)
*C07C 323/52* (2006.01)
*C07C 323/58* (2006.01)

(52) U.S. Cl.
CPC .......... *C07C 323/52* (2013.01); *C07C 323/58* (2013.01); *C07F 19/005* (2013.01); *C07C 229/06* (2013.01); *G01N 23/20075* (2013.01)

(58) Field of Classification Search
None
See application file for complete search history.

(56) References Cited

U.S. PATENT DOCUMENTS

| 3,272,860 | A | 9/1966 | Nufer |
| 4,335,257 | A | 6/1982 | Cummins et al. |
| 4,579,962 | A | 4/1986 | Takano |
| 6,287,627 | B1 | 9/2001 | Binder et al. |
| 8,962,884 | B2 | 2/2015 | Le Thiesse et al. |
| 9,718,769 | B2 | 8/2017 | Buisson et al. |

FOREIGN PATENT DOCUMENTS

| DE | 197 07 380 A1 | 8/1998 |
| EP | 0 049 057 A1 | 4/1982 |
| EP | 0 140 865 A1 | 5/1985 |
| FR | 2 964 968 A1 | 3/2012 |
| WO | 2013/136030 A2 | 9/2013 |

OTHER PUBLICATIONS

Romoser, G., et al., "An Evaluation of the L-Methionine Activity of the Hydroxy Analogue of Methionine," Poult Sci., vol. 55, No. 3, 1976, pp. 1099-1103.
International Search Report issued in Application No. PCT/FR2016/050620, dated Jun. 6, 2016.

*Primary Examiner* — Robert A Wax
*Assistant Examiner* — Randeep Singh
(74) *Attorney, Agent, or Firm* — Young & Thompson

(57) ABSTRACT

Disclosed are pulverulent compositions of a complex between an acid and a metal, having a high organosulfur compound content, and method for preparing same.

20 Claims, 9 Drawing Sheets

A                                              B

A                                              B

PULVERULENT COMPOSITIONS OF A COMPLEX BETWEEN AN ACID AND A METAL HAVING A HIGH ORGANOSULFUR COMPOUND CONTENT AND METHOD FOR PREPARING SAME

The present invention relates to pulverulent compositions of a complex between an acid and a metal, having a high organosulfur compound content, and to the process for producing same.

Methionine, which is an essential amino acid, and 2-hydroxy-4-methylthiobutanoic acid (HMTBA), which is a methionine analog, have widespread applications in human beings as a food supplement or a medicament, and also in animal nutrition. Their metal salts, for example calcium, magnesium or zinc salts, in solid form, are advantageous since they make it possible to make up for deficiencies in elements or trace elements. The most well-known salt of HMTBA is the dicalcium salt, comprising two mol of HMTBA equivalent per mole of calcium, corresponding to the formula $(HMTBA)_2Ca$.

Numerous examples describe the production of salts of methionine or of a methionine analog, in particular HMTBA.

In the case of HMTBA, while the concentrated acid product is encountered in liquid form, and high concentration often greater than 87% of HMTBA, the salts are in solid form and are less concentrated in terms of HMTBA due to the introduction of the cation(s) used for the formation of the salt.

Most of the pulverulent forms have a composition corresponding to the stoichiometry of the dicalcium salt $(HMTBA)_2Ca$.

Thus, U.S. Pat. No. 4,335,257 describes the preparation of the salt of formula $(HMTBA)_2Ca$ which makes it possible to obtain a composition in solid form which provides no more than 85% of HMTBA in its composition by weight.

U.S. Pat. No. 3,272,860, EP 0 049 057, U.S. Pat. No. 6,287,627 and FR 2 964 968 thus describe the obtaining of salts of formula $(HMTBA)_2Ca$ obtained from HMTBA which are all in stoichiometric proportions and thus at maximum HMTBA contents of 80% to 87%.

Few prior art documents report the obtaining of compositions containing an HMTBA content greater than that the stoichiometric proportion of the formation of the dicalcium salt $(HMTBA)_2Ca$.

Romoser and al (Poult. Sci. 1976, 55(3), pp 1099-1103) obtain a composition rich in HMA in the acid form (HMTBA) by spraying said acid form onto a solid support (vermiculite). However, the HMTBA content is in this case only 50%.

Likewise, EP 140865 describes the obtaining of calcium salts of HMTBA consisting of more than two and less than ten mol of HMTBA equivalent per mol of calcium. These salts are obtained by reacting HMTBA with a calcium source chosen from calcium oxide (CaO), calcium hydroxide $(Ca(OH)_2)$, calcium carbonate $(CaCO_3)$ and also an HMTBA salt, for example the salt $(HMTBA)_2$ Ca. HMTBA is generally in highly concentrated aqueous solution, with which the calcium salt is mixed, and then the reaction medium thus obtained is dried at a temperature of about 70° C.

The product obtained is at 94% of HMTBA equivalent. However, the reaction medium of HMTBA with the calcium source is very viscous and tacky; it is therefore very difficult to homogenize in mixers or reactors equipped with conventional stirring systems and, at the end of the reaction, it is necessary to perform in-situ drying order to be able to empty the reactor. It also requires a step of forming after drying, by milling, and then sieving. Finally, this process, which is necessarily batchwise, does not allow a continuous process adaptation.

Recycling of HMTBA calcium salt, for example of $(HMTBA)_2Ca$, to the calcium source before adding the HMTBA makes it possible to improve the consistency of the reaction medium and facilitates the implementation of the process. However, as described in U.S. Pat. No. 4,335,257 this improvement requires a weight provision of at least 20% of said salt and up to 80% of said salt. Because of this requirement, this process reduces the productivity and increases the overdimensioning of facilities.

Thus, one objective of the present invention consists in providing complexes between an acid and a metal in solid pulverulent form having an organosulfur compound content, in particular HMTBA content, greater than 87%.

Another objective of the invention consists in providing complexes between an acid and a metal, in the form of stable powders, that can be easily handled and are suitable for the application for which said complexes are intended.

Another objective of the invention consists in providing a process for producing a complex between an acid and a metal, batchwise, without difficulties in terms of sticking or the appearance of a viscous mass during the production, and without the use of a vessels heal for preparing the product.

Another objective of the invention consists in providing a process for producing complexes between an acid and a metal, continuously. Consequently, a subject of the invention is a particle comprising:

a core consisting essentially of a salt of formula (I) below:

$$(A^-)_n M^{n+} \qquad (I)$$

in which:

$A^-$ represents an anion chosen from the group consisting of 2-hydroxy-4-methylthiobutanoate, methioniate and cysteinate, M represents a divalent or trivalent metal, n being equal to 2 when said metal is divalent and to 3 when said metal is trivalent, and a layer comprising a compound B chosen from the group consisting of 2-hydroxy-4-methylthiobutanoic acid (HMTBA), methionine, cysteine, mixtures thereof, salts thereof and complexes thereof, said layer coating said core, the weight percentage of said compound B relative to the salt of formula (I) of the core being from approximately 10% to approximately 50%, said compound B not being, or not only being, in the form of a salt of formula (I), the organosulfur compound content (TOS) of said particle being greater than 87% by weight, in particular greater than 88%, 89% or 90% by weight, relative to the total weight of said particle.

The organosulfur compound content corresponds to the TOS (Total Organic Sulfur).

When the particle comprises HMTBA, the HMTBA content is measured by measuring the TOS.

Surprisingly, the particle obtained is stable and remains in pulverulent form, despite high TOSs. It is neither viscous nor tacky.

The term "particle" is intended to mean a small element of matter which, to the naked eye, appears to be one piece and not made up of a juxtaposition of smaller elements.

The term "core consisting essentially of a salt of formula (I)" is intended to mean in particular a core comprising more than 70% by weight of said salt of formula (I).

The weight percentage of said compound B included in said layer is given relative to the weight of salt of formula (I) of the core, and not relative to the total weight of said particle.

The term "said compound B is not, or not only being, in the form of a salt of formula (I)", is intended to mean that the compound B is in a form other than a salt of formula (I), for example in free form or in the form of a complex of formula (II) as described hereinafter, or in the form of a mixture comprising a salt of formula (I) and at least one other form such as the free form or a complex of formula (II).

According to one advantageous embodiment, the present invention relates to a particle as defined above, in which said compound B is in the:
- free form, chosen from 2-hydroxy-4-methylthiobutanoic acid (HMTBA), methionine and cysteine, and/or
- form of said salt of formula (I) as defined above, and/or
- form of a complex of formula $(A)_4M$ (II) in which A and M are as defined above, A preferably representing 2-hydroxy-4-methylthiobutanoic acid (HMTBA), said compound B not being, or not only being, in the form of a salt of formula (I),
said compound B being in particular in the:
- free form,
- form of the complex of formula (II),
- form of a mixture of the free form and of the complex of formula (II),
- form of a mixture of the free form and of salt of formula (I),
- form of a mixture of the salt of formula (I) and of the complex of formula (II), or
- form of a mixture of the free form, of the salt of formula (I) and of the complex of formula (II).

According to one advantageous embodiment, the present invention relates to a particle as defined above, in which said compound B is in the:
- form of the complex of formula (II),
- form of a mixture of the free form and of the complex of formula (II),
- form of a mixture of the salt of formula (I) and of the complex of formula (II), or
- form of a mixture of the free form, of the salt of formula (I) and of the complex of formula (II), said compound B being in particular in the form of the complex of formula (II).

According to one advantageous embodiment, the present invention relates to a particle as defined above, comprising less than 3%, in particular less than 2% or 1.5%, of water by weight.

According to one advantageous embodiment, the present invention relates to a particle as defined above, the calcium content of which is from 6% to 11% by weight, in particular from 6.5% to 10%, especially from 7% to 9%, even more especially is 7.5%, 8,0% or 8.5%, the calcium content being in particular approximately 8%.

According to one advantageous embodiment, the present invention relates to a particle as defined above, in which the weight percentage of said compound B relative to the salt of formula (I) of the core is from approximately 10% to approximately 40%, in particular from approximately 15% to approximately 35%, especially from approximately 20% to approximately 32%, even more especially is 21%, 22%, 23%, 24%, 25%, 26%, 27%, 28%, 29%, 30% or 31%.

According to one advantageous embodiment, the present invention relates to a particle as defined above, in which said metal is chosen from the group comprising Mg, Be, Ca, Sr, Ba, Mn, Fe, Co, Ni, Cu, Zn, Pt, B, Al, Ga, In, in particular Mg, Ca, Fe, Mn, Al, Cu, Zn.

According to one advantageous embodiment, the present invention relates to a particle as defined above, in which said metal and n are such that $M^{n+}$ represents $Mg^{2+}$, $Be^{2+}$, $Ca^{2+}$, $Sr^{2+}$, $Ba^{2+}$, $Mn^{2+}$, $Fe^{2+}$, $Fe^{3+}$, $Co^{2+}$, $Co^{3+}$, $Ni^{2+}$, $Ni^{3+}$, $Cu^{2+}$, $Zn^{2+}$, $Pt^{2+}$, $Al^{3+}$, $Ga^{3+}$ or $In^{3+}$, in particular $Mg^{2+}$, $Ca^{2+}$, $Fe^{2+}$, $Fe^{3+}$, $Al^{3+}$, $Mn^{2+}$, $Cu^{2+}$ or $Zn^{2+}$.

According to one advantageous embodiment, the present invention relates to a particle as defined above, in which said salt of formula (I) is $(HMTBA)_2Ca$, $(HMTBA)_2Mg$, $(HMTBA)_2Fe$, $(HMTBA)_2Mn$, $(HMTBA)_2Zn$, $(HMTBA)_2Cu$, $(HMTBA)_3Fe$, $(HMTBA)_3Al$, $(Methionine)_2Ca$, $(Methionine)_2Mg$, $(Methionine)_2Fe$, $(Methionine)_2Mn$, $(Methionine)_2Zn$, $(Methionine)_2Cu$, $(Methionine)_3Fe$, $(Methionine)_3Al$, $(Cysteine)_2Ca$, $(Cysteine)_2Mg$, $(Cysteine)_2Fe$, $(Cysteine)_2Mn$, $(Cysteine)_2Zn$, $(Cysteine)_2Cu$, $(Cysteine)_3Fe$, or $(Cysteine)_3Al$, even especially a salt of formula $(HMTBA)_2Ca$, $(HMTBA)_2Mg$, $(HMTBA)_2Fe$, $(HMTBA)_2Mn$, $(HMTBA)_2Zn$, $(HMTBA)_2Cu$, $(Methionine)_2Ca$, $(Methionine)_2Mg$, $(Methionine)_2Fe$, $(Methionine)_2Mn$, $(Methionine)_2Zn$, $(Methionine)_2Cu$, $(Cysteine)_2Ca$, $(Cysteine)_2Mg$, $(Cysteine)_2Fe$, $(Cysteine)_2Mn$, $(Cysteine)_2Zn$ or $(Cysteine)_2Cu$.

According to one advantageous embodiment, the present invention relates to a particle as defined above, in which said anion $A^-$ is 2-hydroxy-4-methylthiobutanoate.

According to one advantageous embodiment, the present invention relates to a particle as defined above, in which said compound B included in said layer is 2-hydroxy-4-methylthiobutanoic acid (HMTBA), or a salt or complex thereof.

According to one advantageous embodiment, the present invention relates to a particle as defined above, in which said anion $A^-$ is 2-hydroxy-4-methylthiobutanoate, and said compound B included in said layer is 2-hydroxy-4-methylthiobutanoic acid (HMTBA), or a salt or complex thereof.

According to one advantageous embodiment, the present invention relates to a particle as defined above, in which the compound A forming said anion $A^-$ and said compound B, if B is in free form, or the compound forming the compound B, if B is in the form of a salt or of a complex, are different.

According to one advantageous embodiment, the present invention relates to a particle as defined above, in which said 2-hydroxy-4-methylthiobutanoic acid (HMTBA) is more than 60% by weight in monomeric form.

According to one advantageous embodiment, the present invention relates to a particle comprising:
- a core consisting essentially of salt of formula (I) $(HMTBA)_2Ca$, and
- a layer comprising a compound B chosen from the group consisting of 2-hydroxy-4-methylthiobutanoic acid (HMTBA), methionine, cysteine, mixtures thereof, salts thereof and complexes thereof, said layer coating said core,
the weight percentage of said compound B relative to the salt of formula (I) $(HMTBA)_2Ca$ of the core being from approximately 10% to approximately 50%,
said compound B not being, or not only being, in the form of the salt of formula (I) $(HMTBA)_2Ca$,
the organosulfur compound content (TOS) of said particle being greater than 87% by weight, in particular greater than 88%, 89% or 90% by weight, relative to the total weight of said particle.

According to one advantageous embodiment, the present invention relates to a particle comprising:
- a core consisting essentially of salt of formula (I) (HMTBA)$_2$Ca, and
- a layer comprising 2-hydroxy-4-methylthiobutanoic acid (HMTBA), said layer coating said core,
the weight percentage of the HMTBA of said layer relative to the salt of formula (I) (HMTBA)$_2$Ca of the core being from approximately 10% to approximately 50%,
the HMTBA of said layer not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle.

According to one advantageous embodiment, the present invention relates to a particle comprising:
- a core consisting essentially of salt of formula (I) (HMTBA)$_2$Ca, and
- a layer comprising 2-hydroxy-4-methylthiobutanoic acid (HMTBA) and calcium, the S/Ca atomic ratio being from 2.7 to 3.7, said layer coating said core,
the weight percentage of the HMTBA of said layer relative to the salt of formula (I) (HMTBA)$_2$Ca of the core being from approximately 10% to approximately 50%,
the organosulfur compound content (TOS) of said particle being greater than 87% by weight, in particular greater than 88%, 89% or 90% by weight, relative to the total weight of said particle.

According to one advantageous embodiment, the present invention relates to a particle comprising:
- a core consisting essentially of salt of formula (I) (HMTBA)$_2$Ca, and
- a layer comprising complex of formula (II) (HMTBA)$_4$Ca, said layer coating said core,
the weight percentage of the HMTBA of said layer relative to the salt of formula (I) (HMTBA)$_2$Ca of the core being from approximately 10% to approximately 50%,
the organosulfur compound content (TOS) of said particle being greater than 87% by weight, in particular greater than 88%, 89% or 90% by weight, relative to the total weight of said particle.

The invention also relates to a pulverulent composition consisting of or comprising particles as defined above.

The term "pulverulent composition of particles" is intended to mean a solid, in a fractionated state, that is to say consisting of particles, according to the present invention.

According to one advantageous embodiment, the present invention relates to a composition as defined above, in which the particle size of said particles ranges from 10 to 3000 µm, in particular from 20 to 300 µm, especially from 100 to 250 µm, in terms of mean particle size [Dv(0,5)].

The term "mean particle size [Dv(0,5)]" is intended to mean the mean particle size diameter, measured by laser diffraction, 50% of the particles of said composition having a diameter greater than said mean diameter and 50% of the particles of said composition having a diameter less than said mean diameter.

According to one advantageous embodiment, the present invention relates to a composition as defined above, the bulk density of which is greater than 350 g/L, in particular greater than 400 g/L.

The bulk (or loose packed) density of said pulverulent composition can be measured using a 250 ml cylinder that is graduated every 2 ml. This method is described in standard AFNOR NF X 04-344. The procedure consists in pouring the pulverulent composition into the cylinder so as to be close to the maximum graduation of the container and then measuring the weight and also the volume occupied by said pulverulent composition. The bulk density is then calculated by the ratio of the weight of powder to the volume occupied by the pulverulent composition According to one advantageous embodiment, the present invention relates to a composition as defined above, the tapped density of which after 10 taps is greater than 400 g/L, in particular greater than 450 g/L.

The tapped density of said pulverulent composition can be measured using a 250 ml cylinder graduated every 2 ml and also a Dual Autotap volumenometer in accordance with standards ASTM B527 and D4164. The procedure consists in pouring the pulverulent composition into the cylinder so as to be close to the maximum graduation of the container. The cylinder is then carefully placed on the tray of the Autotap where it is subjected to the desired number of vertical shapes as a function of the desired tapped density (D10=tapped density at 10 taps, D500=tapped density at 500 taps). The tapped density is then calculated by the ratio of the weight of tapped powder to the volume occupied by said tapped powder in said cylinder.

According to one advantageous embodiment, the present invention relates to a composition as defined above, the angle of repose of which is from 34° to 40°, in particular from 36° to 38°.

The angle of repose of said pulverulent composition can be measured by determining the angle at the base of the cone of fallen material obtained by passing the sample through a special funnel (stainless steel funnel, of which the base of the internal diameter (d) is 6 mm) at a conventional height, above a perfectly flat and horizontal marble plate. The procedure, carried out four times, consists in:
- adjusting the height (H) between the plate and the base of the funnel to 40 mm,
- confirming the perpendicularity of the center of the funnel with the marble plate,
- placing the sheet of paper on the plate while centering it with the funnel,
- pouring the powder into the funnel,
- halting the feeding when the tip of the cone touches the base of the funnel,
- drawing the base of the cone, in the shape of a circle, in a square,
- measuring the distance D separating two opposite sides of said square.

The angle of repose for the fallen material α is expressed in degrees and is given by the formula $$\alpha = \text{Arctg}\frac{2H}{D-d}$$

with
H: the height of the cone in mm (H=40),
d: internal diameter of the base of the funnel in mm (d=6 mm),
D: arithmetic mean of the four measurements in mm.

According to one advantageous embodiment, the present invention relates to a composition as defined above, comprising, in addition to said particles, oil, in particular vegetable oil.

The vegetable oil is particularly chosen from soybean oil, sunflower oil, rapeseed oil, groundnut oil and mixtures thereof.

The invention also relates to a process for producing a particle comprising:

a core consisting essentially of a salt of formula (I) below:

$$(A^-)_n M^{n+} \quad (I)$$

in which:

A⁻ represents an anion chosen from the group consisting of 2-hydroxy-4-methylthiobutanoate, methioniate and cysteinate, M represents a divalent or trivalent metal, n being equal to 2 when said metal is divalent and to 3 when said metal is trivalent, and a layer comprising a compound B chosen from the group consisting of 2-hydroxy-4-methylthiobutanoic acid (HMTBA), methionine, cysteine, mixtures thereof, salts thereof and complexes thereof, said layer coating said core, the weight percentage of said compound B relative to the salt of formula (I) of the core being from approximately 10% to approximately 50%, said compound B not being, or not only being, in the form of a salt of formula (I), the organosulfur compound content (TOS) of said particle being greater than 87% by weight, in particular greater than 88%, 89% or 90% by weight, said process comprising a step of spraying, onto a solid consisting essentially of a salt of formula (I) as defined above, a composition comprising a compound B chosen from the group consisting of 2-hydroxy-4-methylthiobutanoic acid (HMTBA), methionine, cysteine, mixtures thereof, salts thereof and complexes thereof, the weight of said compound B being from approximately 10% to approximately 50% of the weight of the salt of formula (I) of the solid, in order to obtain said particle.

According to one advantageous embodiment, the present invention relates to a process as defined above, wherein said composition comprises a compound B chosen from the group consisting of 2-hydroxy-4-methylthiobutanoic acid (HMTBA), methionine and cysteine, in free form.

According to one advantageous embodiment, the present invention relates to a process as defined above, wherein said spraying step is carried out:

batchwise or continuously in a fluidized airbed, or in a spray tower by co-spraying.

The term "co-spraying" is intended to mean the joint spraying of a liquid and of a powder.

According to one advantageous embodiment, the present invention relates to a process as defined above, wherein said spraying step is carried out continuously.

According to one advantageous embodiment, the present invention relates to a process as defined above, wherein said spraying step is carried out on a vibro-fluidizer.

According to one advantageous embodiment, the present invention relates to a process as defined above, wherein said spraying step is carried out under an inert atmosphere, in particular under nitrogen, the inert gas being especially recycled.

According to one advantageous embodiment, the present invention relates to a process as defined above, wherein said composition is in liquid form.

According to one advantageous embodiment, the present invention relates to a process as defined above, wherein said composition also comprises water, the weight percentage of water of said composition being from 0.5 to 50.

According to one advantageous embodiment, the present invention relates to a process as defined above, wherein the core consisting essentially of a salt of formula (I) is obtained by reactive atomization.

The term "reactive atomization" is intended to mean the atomization of a reaction mixture, said mixture being the combination of two or more compounds which can chemically react together when they are mixed, the bringing of the compounds of the reaction mixture into contact being immediately followed by the spraying by atomization.

According to one advantageous embodiment, the present invention relates to a process as defined above, wherein the core consisting essentially of a salt of formula (I) is obtained in a fluidized airbed, in a granulator, in a rotary granulator, or in a mixer.

According to one advantageous embodiment, the present invention relates to a process as defined above, wherein the core consisting essentially of a salt of formula (I) is obtained by reactive extrusion.

The reactive extrusion can be carried out by techniques well known to those skilled in the art. In particular, the salt of formula (I) can be obtained by the reactive extrusion as described in application FR 2 964 968.

According to one advantageous embodiment, the present invention relates to a process as defined above, wherein the core consisting essentially of a salt of formula (I) is obtained using a static or dynamic mixer.

According to one advantageous embodiment, the present invention relates to a process as defined above, wherein the core consisting essentially of a salt of formula (I) is obtained by reactive atomization under an inert atmosphere, in particular under nitrogen, the inert gas being in particular recycled when the core consisting essentially of a salt of formula (I) is not obtained by reactive extrusion.

According to one advantageous embodiment, the present invention relates to a process as defined above, wherein said compound B included in said layer is in:

free form, chosen from 2-hydroxy-4-methylthiobutanoic acid (HMTBA), methionine and cysteine, and/or form of salt of said formula (I) as defined above, and/or form of a complex of formula $(A)_4M$ (II) in which A and M are as defined above, A preferably representing 2-hydroxy-4-methylthiobutanoic acid (HMTBA), said compound B not being, or not only being, in the form of a salt of formula (I), said compound B being in particular in the:

free form, form of the complex of formula (II), form of a mixture of the free form and form of the complex of formula (II), form of a mixture of the free form and of the salt of formula (I), form of a mixture of the salt of formula (I) and of the complex of formula (II), or form of a mixture of the free form, of the salt of formula (I) and of the complex of formula (II).

According to one advantageous embodiment, the present invention relates to a process as defined above, wherein said particle comprises less than 3%, 2% or 1.5%, of water by weight According to one advantageous embodiment, the present invention relates to a process as defined above, wherein said particle has a calcium content from 6% to 11% by weight, in particular from 6.5% to 10%, especially from 7% to 9%, the calcium content being in particular approximately 8%.

According to one advantageous embodiment, the present invention relates to a process as defined above, wherein the weight percentage of said compound B relative to the salt of formula (I) of the core is from approximately 10% to approximately 40%, in particular from approximately 15% to approximately 35%, especially from approximately 20% to approximately 32%.

According to one advantageous embodiment, the present invention relates to a process as defined above, wherein said metal is chosen from the group comprising Mg, Be, Ca, Sr, Ba, Mn, Fe, Co, Ni, Cu, Zn, Pt, B, Al, Ga, In, in particular Mg, Ca, Fe, Mn, Al, Cu, Zn.

According to one advantageous embodiment, the present invention relates to a process as defined above, wherein said metal and n are such that $M^{n+}$ represents $Mg^{2+}$, $Be^{2+}$, $Ca^{2+}$, $Sr^{2+}$, $Ba^{2+}$, $Mn^{2+}$, $Fe^{2+}$, $Fe^{3+}$, $Co^{2+}$, $Co^{3+}$, $Ni^{2+}$, $Ni^{3+}$, $Cu^{2+}$, $Zn^{2+}$, $Pt^{2+}$, $Al^{3+}$, $Ga^{3+}$ or $In^{3+}$, in particular $Mg^{2+}$, $Ca^{2+}$, $Fe^{2+}$, $Fe^{3+}$, $Al^{3+}$, $Mn^{2+}$, $Cu^{2+}$ or $Zn^{2+}$.

According to one advantageous embodiment, the present invention relates to a process as defined above, wherein said salt of formula (I) is $(HMTBA)_2Ca$, $(HMTBA)_2Mg$, $(HMTBA)_2Fe$, $(HMTBA)_2Mn$, $(HMTBA)_2Zn$, $(HMTBA)_2Cu$, $(HMTBA)_3Fe$, $(HMTBA)_3Al$, $(Methionine)_2Ca$, $(Methionine)_2Mg$, $(Methionine)_2Fe$, $(Methionine)_2Mn$, $(Methionine)_2Zn$, $(Methionine)_2Cu$, $(Methionine)_3Fe$, $(Methionine)_3Al$, $(Cysteine)_2Ca$, $(Cysteine)_2Mg$, $(Cysteine)_2Fe$, $(Cysteine)_2Mn$, $(Cysteine)_2Zn$, $(Cysteine)_2Cu$, $(Cysteine)_3Fe$, or $(Cysteine)_3Al$, even more especially a salt of formula $(HMTBA)_2Ca$, $(HMTBA)_2Mg$, $(HMTBA)_2Fe$, $(HMTBA)_2Mn$, $(HMTBA)_2Zn$, $(HMTBA)_2Cu$, $(Methionine)_2Ca$, $(Methionine)_2Mg$, $(Methionine)_2Fe$, $(Methionine)_2Mn$, $(Methionine)_2Zn$, $(Methionine)_2Cu$, $(Cysteine)_2Ca$, $(Cysteine)_2Mg$, $(Cysteine)_2Fe$, $(Cysteine)_2Mn$, $(Cysteine)_2Zn$ or $(Cysteine)_2Cu$.

According to one advantageous embodiment, the present invention relates to a process as defined above, wherein said anion $A^-$ is 2-hydroxy-4-methylthiobutanoate.

According to one advantageous embodiment, the present invention relates to a process as defined above, wherein said compound B included in said layer is 2-hydroxy-4-methylthiobutanoic acid (HMTBA), or a salt or complex thereof.

According to one advantageous embodiment, the present invention relates to a process as defined above, wherein said anion $A^-$ is 2-hydroxy-4-methylthiobutanoate, and said compound B included in said layer is 2-hydroxy-4-methylthiobutanoic acid (HMTBA), or a salt or complex thereof.

According to one advantageous embodiment, the present invention relates to a process as defined above, wherein said 2-hydroxy-4-methylthiobutanoic acid (HMTBA) is more than 60% by weight in monomeric form.

According to one advantageous embodiment, the present invention relates to a process for producing a particle comprising:
  a core consisting essentially of salt of formula (I) $(HMTBA)_2Ca$, and
  a layer comprising a compound B chosen from the group consisting of 2-hydroxy-4-methylthiobutanoic acid (HMTBA), methionine, cysteine, mixtures thereof, salts thereof and complexes thereof,
said layer coating said core,
the weight percentage of said compound B relative to the salt of formula (I) $(HMTBA)_2Ca$ of the core being from approximately 10% to approximately 50%,
said compound B not being, or not only being, in the form of the salt of formula (I) $(HMTBA)_2Ca$,
the organosulfur compound content (TOS) of said particle being greater than 87% by weight, in particular greater than 88%, 89% or 90% by weight, relative to the total weight of said particle,
said process comprising a step of spraying, onto a solid consisting essentially of salt of formula (I) $(HMTBA)_2Ca$, a composition comprising a compound B chosen from the group consisting of 2-hydroxy-4-methylthiobutanoic acid (HMTBA), methionine, cysteine, mixtures thereof, salts thereof and complexes thereof, the weight of said compound B being from approximately 10% to approximately 50% of the weight of the salt of formula (I) of the solid, in order to obtain said particle.

According to one advantageous embodiment, the present invention relates to a process for producing a particle comprising:
  a core consisting essentially of salt of formula (I) $(HMTBA)_2Ca$, and
  a layer comprising a compound B chosen from the group consisting of 2-hydroxy-4-methylthiobutanoic acid (HMTBA), methionine, cysteine, mixtures thereof, salts thereof and complexes thereof,
said layer coating said core,
the weight percentage of said compound B relative to the salt of formula (I) $(HMTBA)_2Ca$ of the core being from approximately 10% to approximately 50%,
said compound B not being, or not only being, in the form of the salt of formula (I) $(HMTBA)_2Ca$,
the organosulfur compound content (TOS) of said particle being greater than 87% by weight, in particular greater than 88%, 89% or 90% by weight, relative to the total weight of said particle,
said process comprising a step of batchwise or continuous spraying in a fluidized airbed onto a solid consisting essentially of salt of formula (I) $(HMTBA)_2Ca$, of a composition comprising a compound B chosen from the group consisting of 2-hydroxy-4-methylthiobutanoic acid (HMTBA), methionine, cysteine, mixtures thereof, salts thereof and complexes thereof, the weight of said compound B being from approximately 10% to approximately 50% of the weight of the salt of formula (I) of the solid, in order to obtain said particle.

According to one advantageous embodiment, the present invention relates to a process for producing a particle comprising:
  a core consisting essentially of salt of formula (I) $(HMTBA)_2Ca$, and
  a layer comprising a compound B chosen from the group consisting of 2-hydroxy-4-methylthiobutanoic (HMTBA), methionine, cysteine, mixtures thereof, salts thereof and complexes thereof,
said layer coating said core,
the weight percentage of said compound B relative to the salt of formula (I) $(HMTBA)_2Ca$ of the core being from approximately 10% to approximately 50%,
said compound B not being, or not only being, in the form of the salt of formula (I) $(HMTBA)_2Ca$,
the organosulfur compound content (TOS) of said particle being greater than 87% by weight, in particular greater than 88%, 89% or 90% by weight, relative to the total weight of said particle,
said process comprising a step of batchwise or continuous spraying in a fluidized airbed onto a solid consisting essentially of salt of formula (I) $(HMTBA)_2Ca$, said solid being obtained by reactive atomization, of a composition comprising a compound B chosen from the group consisting of 2-hydroxy-4-methylthiobutanoic acid (HMTBA), methionine, cysteine, mixtures thereof, salts thereof and complexes thereof, the weight of said compound B being from approximately 10% to approximately 50% of the weight of the salt of formula (I) of the solid, in order to obtain said particle.

According to one advantageous embodiment, the present invention relates to a process for producing a particle comprising:
- a core consisting essentially of salt of formula (I) (HMTBA)$_2$Ca, and
- a layer comprising a compound B chosen from the group consisting of 2-hydroxy-4-methylthiobutanoic acid (HMTBA), methionine, cysteine, mixtures thereof, salts thereof and complexes thereof, said layer coating said core,
the weight percentage of said compound B relative to the salt of formula (I) (HMTBA)$_2$Ca of the core being from approximately 10% to approximately 50%,
said compound B not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle,
said process comprising a step of spraying, in a spray tower by co-spraying onto a solid consisting essentially of salt of formula (I) (HMTBA)$_2$Ca, a composition comprising a compound B chosen from the group consisting of 2-hydroxy-4-methylthiobutanoic acid (HMTBA), methionine, cysteine, mixtures thereof, salts thereof and complexes thereof, the weight of said compound B being from approximately 10% to approximately 50% of the weight of the salt of formula (I) of the solid,
in order to obtain said particle.

According to one advantageous embodiment, the present invention relates to a process for producing a particle comprising:
- a core consisting essentially of salt of formula (I) (HMTBA)$_2$Ca, and
- a layer comprising a compound B chosen from the group consisting of 2-hydroxy-4-methylthiobutanoic acid (HMTBA), methionine, cysteine, mixtures thereof, salts thereof and complexes thereof, said layer coating said core,
the weight percentage of said compound B relative to the salt of formula (I) (HMTBA)$_2$Ca of the core being from approximately 10% to approximately 50%,
said compound B not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle,
said process comprising a step of spraying, in a spray tower by co-spraying onto a solid consisting essentially of salt of formula (I) (HMTBA)$_2$Ca, said solid being obtained by reactive atomization in said spray tower, a composition comprising a compound B chosen from the group consisting of 2-hydroxy-4-methylthiobutanoic acid (HMTBA), methionine, cysteine, mixtures thereof, salts thereof and complexes thereof, the weight of said compound B being from approximately 10% to approximately 50% of the weight of the salt of formula (I) of the solid,
in order to obtain said particle.

According to one advantageous embodiment, the present invention relates to a process for producing a particle comprising:
- a core consisting essentially of salt of formula (I) (HMTBA)$_2$Ca, and
- a layer comprising 2-hydroxy-4-methylthiobutanoic acid (HMTBA), said layer coating said core,
the weight percentage of the HMTBA of said layer relative to the salt of formula (I) (HMTBA)$_2$Ca of the core being from approximately 10% to approximately 50%,
the HMTBA of said layer not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle,
said process comprising a step spraying, onto a solid consisting essentially of salt of formula (I) (HMTBA)$_2$Ca, a composition comprising 2-hydroxy-4-methylthiobutanoic acid (HMTBA), the weight of said compound B being from approximately 10% to approximately 50% of the weight of the salt of formula (I) of the solid,
in order to obtain said particle.

According to one advantageous embodiment, the present invention relates to a process for producing a particle comprising:
- a core consisting essentially of salt of formula (I) (HMTBA)$_2$Ca, and
- a layer comprising 2-hydroxy-4-methylthiobutanoic acid (HMTBA), said layer coating said core,
the weight percentage of the HMTBA of said layer relative to the salt of formula (I) (HMTBA)$_2$Ca of the core being from approximately 10% to approximately 50%,
the HMTBA of said layer not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle,
said process comprising a step of batchwise or continuous spraying in a fluidized airbed onto a solid consisting essentially of salt of formula (I) (HMTBA)$_2$Ca, of a composition comprising 2-hydroxy-4-methylthiobutanoic acid (HMTBA), the weight of said compound B being from approximately 10% to approximately 50% of the weight of the salt of formula (I) of the solid,
in order to obtain said particle.

According to one advantageous embodiment, the present invention relates to a process for producing a particle comprising:
- a core consisting essentially of salt of formula (I) (HMTBA)$_2$Ca, and
- a layer comprising 2-hydroxy-4-methylthiobutanoic acid (HMTBA), or a salt or complex thereof, said layer coating said core,
the weight percentage of the HMTBA of said layer relative to the salt of formula (I) (HMTBA)$_2$Ca of the core being from approximately 10% to approximately 50%,
the HMTBA of said layer not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle,
said process comprising a step of batchwise or continuous spraying in a fluidized airbed onto a solid consisting essentially of salt of formula (I) (HMTBA)$_2$Ca, said solid being obtained by reactive atomization, of a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle comprising:
  a core consisting essentially of salt of formula (I) (HMTBA)$_2$Ca, and
  a layer comprising 2-hydroxy-4-methylthiobutanoic acid (HMTBA), or a salt or complex thereof or complexes,
said layer coating said core,
the weight percentage of the HMTBA of said layer relative to the salt of formula (I) (HMTBA)$_2$Ca of the core being from approximately 10% to approximately 50%,
the HMTBA of said layer not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle,
said process comprising a step of spraying, in a spray tower by co-spraying onto a solid consisting essentially of salt of formula (I) (HMTBA)$_2$Ca, a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle comprising:
  a core consisting essentially of salt of formula (I) (HMTBA)$_2$Ca, and
  a layer comprising 2-hydroxy-4-methylthiobutanoic acid (HMTBA), or a salt or complex thereof or complexes,
said layer coating said core,
the weight percentage of the HMTBA of said layer relative to the salt of formula (I) (HMTBA)$_2$Ca of the core being from approximately 10% to approximately 50%,
the HMTBA of said layer not being, or not only being, in the form of the salt of formula (I) (HMTBA)$_2$Ca,
the organosulfur compound content (TOS) of said particle being greater than 87% by weight, in particular greater than 88%, 89% or 90% by weight, relative to the total weight of said particle,
said process comprising a step of spraying, in a spray tower by co-spraying onto a solid consisting essentially of salt of formula (I) (HMTBA)$_2$Ca, said solid being obtained by reactive atomization in said spray tower, a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle comprising:
  a core consisting essentially of salt of formula (I) (HMTBA)$_2$Ca, and
  a layer comprising 2-hydroxy-4-methylthiobutanoic acid (HMTBA) or a salt or complex thereof, and calcium, the S/Ca atomic ratio being from 2.7 to 3.7,
said layer coating said core,
the weight percentage of the HMTBA of said layer relative to the salt of formula (I) of the core being from approximately 10% to approximately 50%,
the organosulfur compound content (TOS) of said particle being greater than 87% by weight, in particular greater than 88%, 89% or 90% by weight, relative to the total weight of said particle,
said process comprising a step spraying, of onto a solid consisting essentially of salt of formula (I) (HMTBA)$_2$Ca, a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle comprising:
  a core consisting essentially of salt of formula (I) (HMTBA)$_2$Ca, and
  a layer comprising 2-hydroxy-4-methylthiobutanoic acid (HMTBA) or a salt or complex thereof, and calcium, the S/Ca atomic ratio being from 2.7 to 3.7,
said layer coating said core,
the weight percentage of the HMTBA of said layer relative to the salt of formula (I) of the core being from approximately 10% to approximately 50%,
the organosulfur compound content (TOS) of said particle being greater than 87% by weight, in particular greater than 88%, 89% or 90% by weight, relative to the total weight of said particle,
said process comprising a step of batchwise or continuous spraying in a fluidized airbed onto a solid consisting essentially of salt of formula (I) (HMTBA)$_2$Ca, of a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle comprising:
  a core consisting essentially of salt of formula (I) (HMTBA)$_2$Ca, and
  a layer comprising 2-hydroxy-4-methylthiobutanoic acid (HMTBA) or a salt or complex thereof, and calcium, the S/Ca atomic ratio being from 2.7 to 3.7,
said layer coating said core,
the weight percentage of the HMTBA of said layer relative to the salt of formula (I) of the core being from approximately 10% to approximately 50%,
the organosulfur compound content (TOS) of said particle being greater than 87% by weight, in particular greater than 88%, 89% or 90% by weight, relative to the total weight of said particle,
said process comprising a step of batchwise or continuous spraying in a fluidized airbed onto a solid consisting essentially of salt of formula (I) (HMTBA)$_2$Ca, said solid being obtained by reactive atomization, of a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle comprising:
  a core consisting essentially of salt of formula (I) (HMTBA)$_2$Ca, and a layer comprising 2-hydroxy-4-methylthiobutanoic acid (HMTBA) or a salt or complex thereof, and calcium, the S/Ca atomic ratio being from 2.7 to 3.7, said layer coating said core, the weight percentage of the HMTBA of said layer relative to the salt of formula (I) of the core being from approximately 10% to approximately 50%, the organosulfur compound content (TOS) of said particle being greater than 87% by weight, in particular greater than 88%, 89% or 90% by weight, relative to the total weight of said particle, said process comprising a step of spraying, in a spray tower by co-spraying onto a solid consisting essentially of salt of formula (I) $(HMTBA)_2Ca$, a composition comprising 2-hydroxy-4-methylthiobutanoic acid (HMTBA), the weight of said HMTBA of said layer being from approximately 10% to approximately 50% of the weight of the salt of formula (I) of the solid, in order to obtain said particle.

According to one advantageous embodiment, the present invention relates to a process for producing a particle comprising:
- a core consisting essentially of salt of formula (I) $(HMTBA)_2Ca$, and
- a layer comprising 2-hydroxy-4-methylthiobutanoic acid (HMTBA) or a salt or complex thereof, and calcium, the S/Ca atomic ratio being from 2.7 to 3.7, said layer coating said core, the weight percentage of the HMTBA of said layer relative to the salt of formula (I) of the core being from approximately 10% to approximately 50%, the organosulfur compound content (TOS) of said particle being greater than 87% by weight, in particular greater than 88%, 89% or 90% by weight, relative to the total weight of said particle, said process comprising a step of spraying, in a spray tower by co-spraying onto a solid consisting essentially of salt of formula (I) $(HMTBA)_2Ca$, said solid being obtained by reactive atomization in said spray tower, a composition comprising 2-hydroxy-4-methylthiobutanoic acid (HMTBA), the weight of said HMTBA of said layer being from approximately 10% to approximately 50% of the weight of the salt of formula (I) of the solid, in order to obtain said particle.

According to one advantageous embodiment, the present invention relates to a process for producing a particle comprising:
- a core consisting essentially of salt of formula (I) $(HMTBA)_2Ca$, and
- a layer comprising complex of formula (II) $(HMTBA)_4Ca$, said layer coating said core, the weight percentage of the HMTBA of said layer relative to the salt of formula (I) of the core being from approximately 10% to approximately 50%, the organosulfur compound content (TOS) of said particle being greater than 87% by weight, in particular greater than 88%, 89% or 90% by weight, relative to the total weight of said particle, said process comprising a step of spraying, onto a solid consisting essentially of salt of formula (I) $(HMTBA)_2Ca$, a composition comprising 2-hydroxy-4-methylthiobutanoic acid (HMTBA), the weight of said HMTBA of said layer being from approximately 10% to approximately 50% of the weight of the salt of formula (I) of the solid, in order to obtain said particle.

According to one advantageous embodiment, the present invention relates to a process for producing a particle comprising:
- a core consisting essentially of salt of formula (I) $(HMTBA)_2Ca$, and
- a layer comprising form of the complex of formula (II) $(HMTBA)_4Ca$, said layer coating said core, the weight percentage of the HMTBA of said layer relative to the salt of formula (I) of the core being from approximately 10% to approximately 50%, the organosulfur compound content (TOS) of said particle being greater than 87% by weight, in particular greater than 88%, 89% or 90% by weight, relative to the total weight of said particle, said process comprising a step of batchwise or continuous spraying in a fluidized airbed onto a solid consisting essentially of salt of formula (I) $(HMTBA)_2Ca$, a composition comprising 2-hydroxy-4-methylthiobutanoic acid (HMTBA), the weight of said HMTBA of said layer being from approximately 10% to approximately 50% of the weight of the salt of formula (I) of the solid, in order to obtain said particle.

According to one advantageous embodiment, the present invention relates to a process for producing a particle comprising:
- a core consisting essentially of salt of formula (I) $(HMTBA)_2Ca$, and
- a layer comprising form of the complex of formula (II) $(HMTBA)_4Ca$, said layer coating said core, the weight percentage of the HMTBA of said layer relative to the salt of formula (I) of the core being from approximately 10% to approximately 50%, the organosulfur compound content (TOS) of said particle being greater than 87% by weight, in particular greater than 88%, 89% or 90% by weight, relative to the total weight of said particle, said process comprising a step of batchwise or continuous spraying in a fluidized airbed onto a solid consisting essentially of salt of formula (I) $(HMTBA)_2Ca$, said solid being obtained by reactive atomization, a composition comprising 2-hydroxy-4-methylthiobutanoic acid (HMTBA), the weight of said HMTBA of said layer being from approximately 10% to approximately 50% of the weight of the salt of formula (I) of the solid, in order to obtain said particle.

According to one advantageous embodiment, the present invention relates to a process for producing a particle comprising:
- a core consisting essentially of salt of formula (I) $(HMTBA)_2Ca$, and
- a layer comprising form of the complex of formula (II) $(HMTBA)_4Ca$, said layer coating said core, the weight percentage of the HMTBA of said layer relative to the salt of formula (I) of the core being from approximately 10% to approximately 50%, the organosulfur compound content (TOS) of said particle being greater than 87% by weight, in particular greater than 88%, 89% or 90% by weight, relative to the total weight of said particle, said process comprising a step of spraying, in a spray tower by co-spraying onto a solid consisting essentially of salt of formula (I) $(HMTBA)_2Ca$, a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle comprising:
 a core consisting essentially of salt of formula (I) (HMTBA)$_2$Ca, and
 a layer comprising form of the complex of formula (II) (HMTBA)$_4$Ca,
said layer coating said core,
the weight percentage of the HMTBA of said layer relative to the salt of formula (I) of the core being from approximately 10% to approximately 50%,
the organosulfur compound content (TOS) of said particle being greater than 87% by weight, in particular greater than 88%, 89% or 90% by weight, relative to the total weight of said particle,
said process comprising a step of spraying, in a spray tower by co-spraying onto a solid consisting essentially of salt of formula (I) (HMTBA)$_2$Ca, said solid being obtained by reactive atomization in said spray tower, a composition comprising 2-hydroxy-4-methylthiobutanoic acid (HMTBA), the weight of said HMTBA of said layer being from approximately 10% to approximately 50% of the weight of the salt of formula (I) of the solid,
in order to obtain said particle.

According to one advantageous embodiment, the present invention relates to a process for producing a particle in which the compound A forming said anion A$^-$ and said compound B, if B is in free form, or the compound forming the compound B, if B is in the form of a salt or of a complex, are different.

According to one advantageous embodiment, the present invention relates to a process for producing a particle in which the compound A forming said anion A$^-$ and said compound B if B is in free form, or the compound forming the compound B, if B is in the form of a salt or of a complex, are different,
said process comprising a step of spraying, onto a solid consisting essentially of a salt of formula (I) $(A^-)_nM^{n+}$ as defined above, of a composition comprising a compound B chosen from the group consisting of 2-hydroxy-4-methylthiobutanoic acid (HMTBA), methionine and cysteine, mixtures thereof, salts thereof and complexes thereof, the weight of said compound B being from approximately 10% to approximately 50% of the weight of the salt of formula (I) of the solid,
in order to obtain said particle.

According to one advantageous embodiment, the present invention relates to a process for producing a particle in which the compound A forming said anion A$^-$ and said compound B if B is in free form, or the compound forming the compound B, if B is in the form of a salt or of a complex, are different.

According to one advantageous embodiment, the present invention relates to a process for producing a particle in which the compound A forming said anion A$^-$ and said compound B, if B is in free form, or the compound forming the compound B, if B is in the form of a salt or of a complex, are different,
said process comprising a step of batchwise or continuous spraying in a fluidized airbed spraying, onto a solid consisting essentially of a salt of formula (I) $(A^-)_nM^{n+}$ as defined above, of a composition comprising a compound B chosen from the group consisting of 2-hydroxy-4-methylthiobutanoic acid (HMTBA), methionine and cysteine, mixtures thereof, salts thereof and complexes thereof, the weight of said compound B being from approximately 10% to approximately 50% of the weight of the salt of formula (I) of the solid, in order to obtain said particle.

According to one advantageous embodiment, the present invention relates to a process for producing a particle in which the compound A forming said anion A$^-$ and said compound B, if B is in free form, or the compound forming the compound B, if B is in the form of a salt or of a complex, are different.

According to one advantageous embodiment, the present invention relates to a process for producing a particle in which the compound A forming said anion A$^-$ and said compound B, if B is in free form, or the compound forming the compound B, if B is in the form of a salt or of a complex, are different,
said process comprising a step of batchwise or continuous spraying in a fluidized airbed, onto a solid consisting essentially of a salt of formula (I) $(A^-)_nM^{n+}$ as defined above, said solid being obtained by reactive atomization, of a composition comprising a compound B chosen from the group consisting of 2-hydroxy-4-methylthiobutanoic acid (HMTBA), methionine and cysteine, mixtures thereof, salts thereof and complexes thereof, the weight of said compound B being from approximately 10% to approximately 50% of the weight of the salt of formula (I) of the solid,
in order to obtain said particle.

According to one advantageous embodiment, the present invention relates to a process for producing a particle in which the compound A forming said anion A$^-$ and said compound B, if B is in free form, or the compound forming the compound B, if B is in the form of a salt or of a complex, are different.

According to one advantageous embodiment, the present invention relates to a process for producing a particle in which the compound A forming said anion A$^-$ and said compound B, if B is in free form, or the compound forming the compound B, if B is in the form of a salt or of a complex, are different,
said process comprising a step of spraying, in a spray tower by co-spraying, onto a solid consisting essentially of a salt of formula (I) $(A^-)_nM^{n+}$ as defined above, of a composition comprising a compound B chosen from the group consisting of 2-hydroxy-4-methylthiobutanoic acid (HMTBA), methionine and cysteine, mixtures thereof, salts thereof and complexes thereof, the weight of said compound B being from approximately 10% to approximately 50% of the weight of the salt of formula (I) of the solid,
in order to obtain said particle.

According to one advantageous embodiment, the present invention relates to a process for producing a particle in which the compound A forming said anion A$^-$ and said compound B, if B is in free form, or the compound forming the compound B, if B is in the form of a salt or of a complex, are different.

According to one advantageous embodiment, the present invention relates to a process for producing a particle in which the compound A forming said anion A$^-$ and said compound B, if B is in free form, or the compound forming the compound B, if B is in the form of a salt or of a complex, are different,
said process comprising a step of spraying, in a spray tower by co-spraying, onto a solid consisting essentially of a salt of formula (I) $(A^-)_nM^{n+}$ as defined above, said solid being obtained by reactive atomization in said spray tower, of a composition comprising a compound B chosen from the group consisting of 2-hydroxy-4-methylthiobutanoic acid (HMTBA), of la methionine and of la cysteine, mixtures thereof, salts thereof and complexes thereof, the weight of said compound B being from approximately 10% to approximately 50% of the weight of the salt of formula (I) of the solid,
in order to obtain said particle.

Sample A corresponds to the powder of salt of formula (I) $(HMTBA)_2Ca$ obtained in the first part of example 9.

Sample B corresponds to the powder obtained at the end of example 1.

Sample C corresponds to the powder obtained at the end of example 12.

Figure 4:
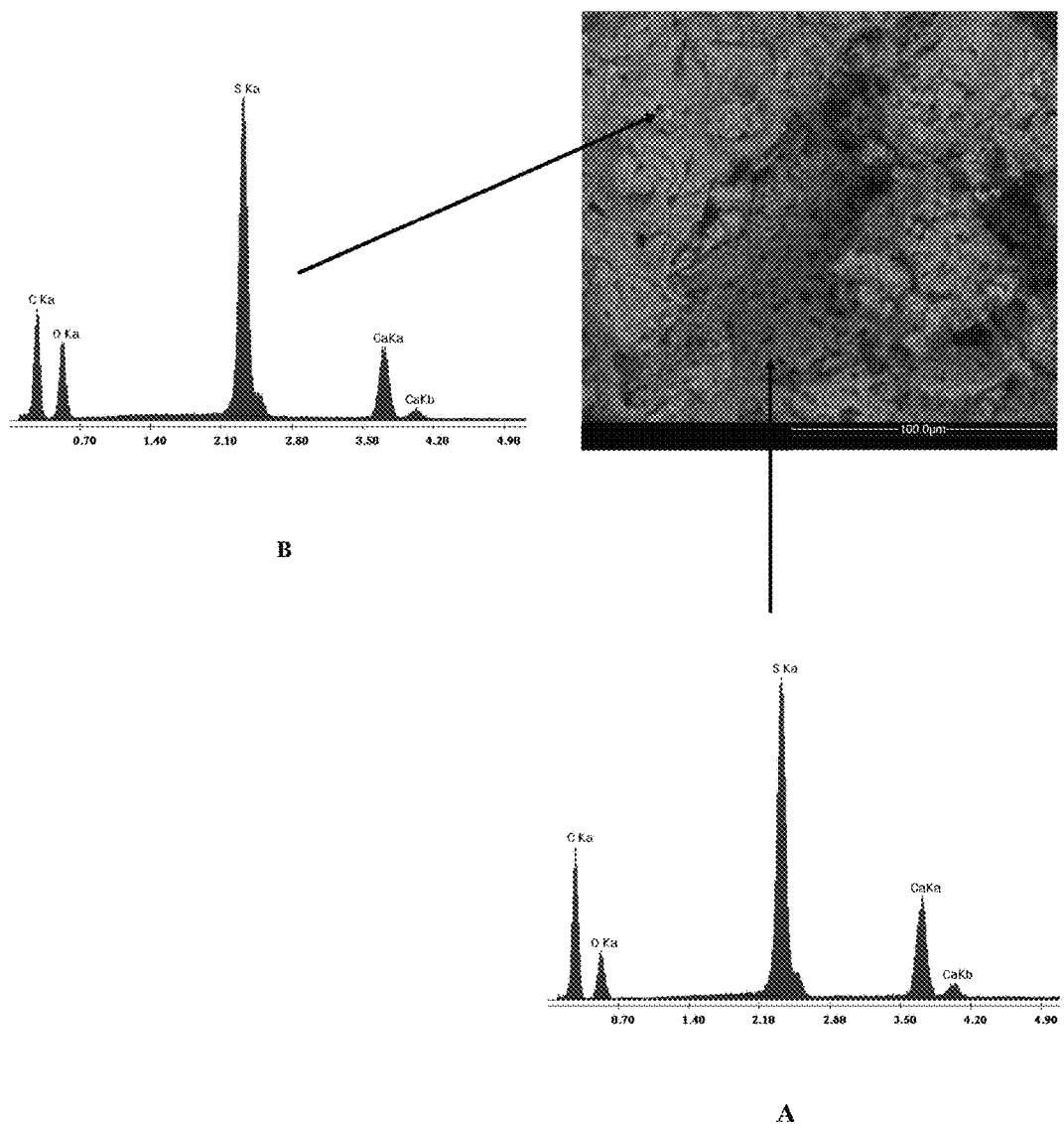

FIG. 4 represents scanning electron microscope (SEM) analysis coupled to X-ray emission spectrometry, carried out at the core (A) and at the surface (B) of one and the same particle according to example 3.

Figure 5:
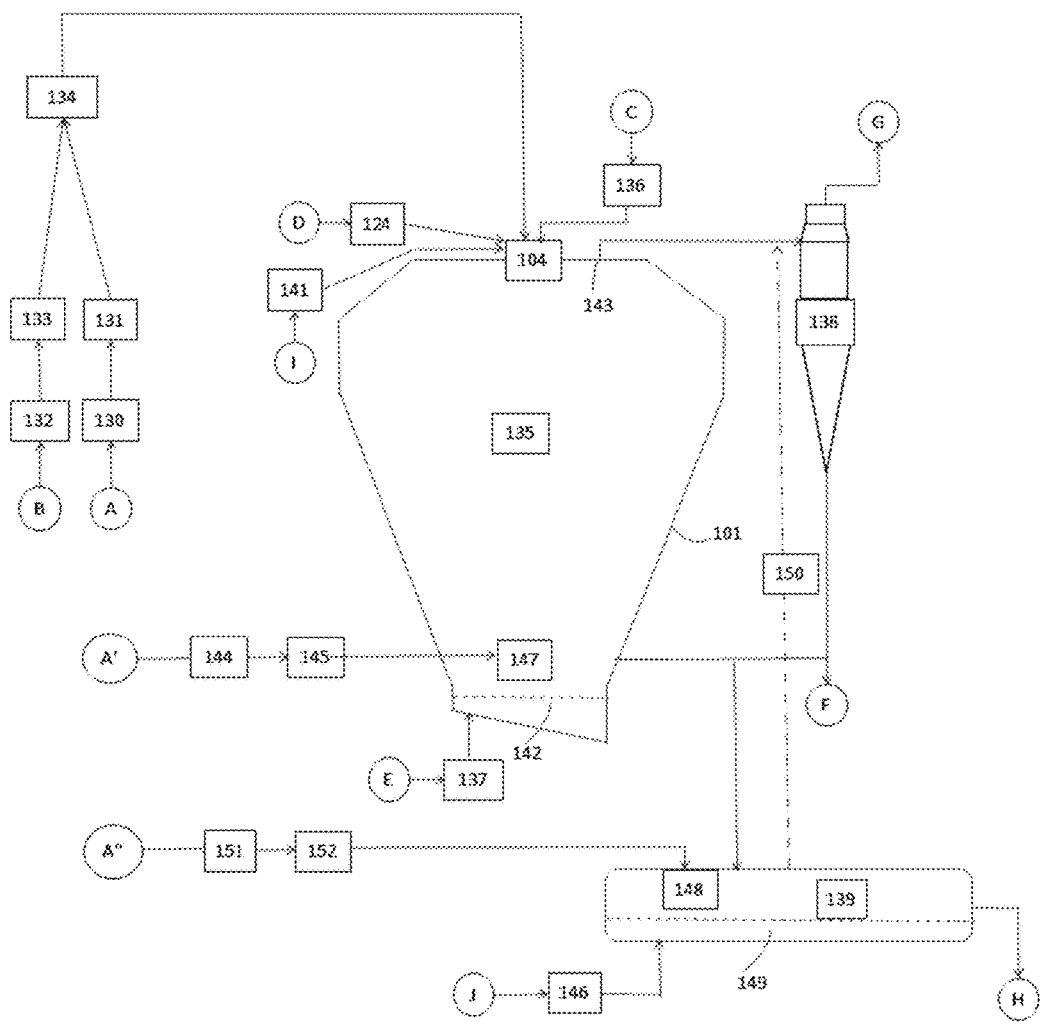

FIG. 5 is a diagram of principle of a process according to the invention, carried out in a multiple effect tower.

An aqueous medium containing an acid, symbolized by the circle A, optionally passes through a heater 130 and feeds, via a pump 131, the contacting device 134. An aqueous medium containing a metal or metal cation symbolized by the circle B optionally passes through a heater 132 and feeds, via a pump 133, the contacting device 134. The aqueous phase resulting from the mixing between the aqueous medium A and the aqueous medium B is sprayed in the spray tower via the spray device 104 intended for the production of monodisperse or polydisperse aerosols.

An aqueous medium containing an acid, symbolized by the circle A', optionally passes through a heater 144 and feeds, via a pump 145 the spraying device 147 intended for the production of aerosols.

An aqueous medium containing an acid, symbolized by the circle A", optionally passes through a heater 151 and feeds, via a pump 152 the spraying device 148 intended for the production of aerosols.

The circle C represents an additional device for spraying anti-agglomerating agent via a powder-metering device 136, if necessary.

The circle D represents the introduction of the hot vector gas, in particular air and/or inert gas, in the spray-drying version, via the fan 124.

The circle E represents the introduction of the secondary vector gas, for the drying and/or the final cooling of the stabilized final composition obtained, which is solid or undergoing solidification, via a fan 137.

The circle J represents the introduction of the vector gas onto the external vibrated fluidized bed 139, for the drying and/or the final cooling of the stabilized final composition obtained, which is solid or undergoing solidification via the fan 146.

A cyclone 138 separates all or some of the final product F that is to say the pulverulent composition, which is recovered, and the vector gas G which is discharged.

The external vibrated fluidized bed 139 allows the recovery of all or some of the final product H, that is to say the pulverulent composition, via the bottom of the tower.

The introduction of the secondary air E takes place through a permeable base 142 of the tower 135 in order to place the powder material in fluidized bed form. The spent air is discharged via one or more orifice(s) 143 made through the upper wall of the chamber 101.

The introduction of the secondary air J takes place through a permeable base 149 of the vibrated fluidized bed 139 in order to place the powder material in fluidized bed form. The spent air is discharged via the line 150 connected to the inlet of the cyclone 138.

Figure 1:
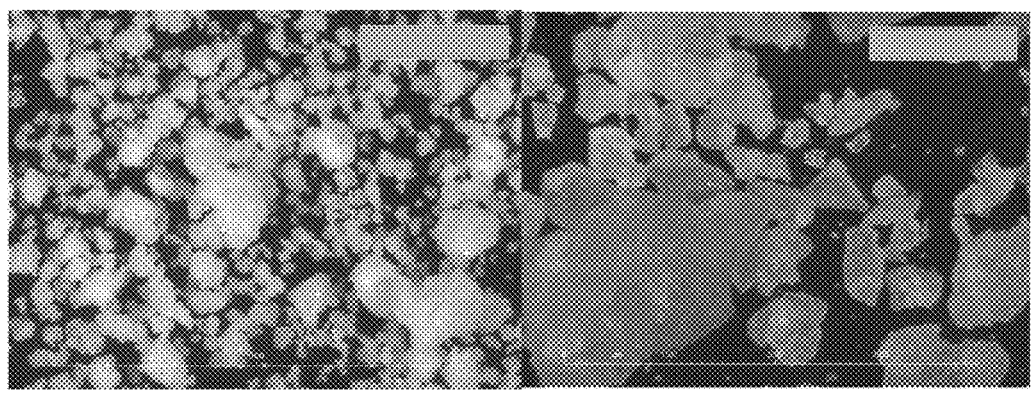
FIG. 1A is an optical microscopy image relating to the powder obtained at the end of example 1.
FIG. 1B is an optical microscopy image relating to the powder obtained at the end of example 12.

In this example, the spent air then passes through the cyclone 138 which produces, on the one hand, particles of product F and, on the other, air to be discharged G. Most of the particles are collected just above the permeable wall 142. FIG. 1 illustrates that the particles are collected either directly in F, or by means of the external fluidized bed 139 in H.

It is also possible to envision the addition, represented by the circle I, in the spray zone, of a powdered substance, in particular fine particles of the pulverulent composition recovered at the outlet of the cyclone 138, product F, or the installation, injected by means of the device 141 consisting mainly of a powder-metering device.

Figure 6:
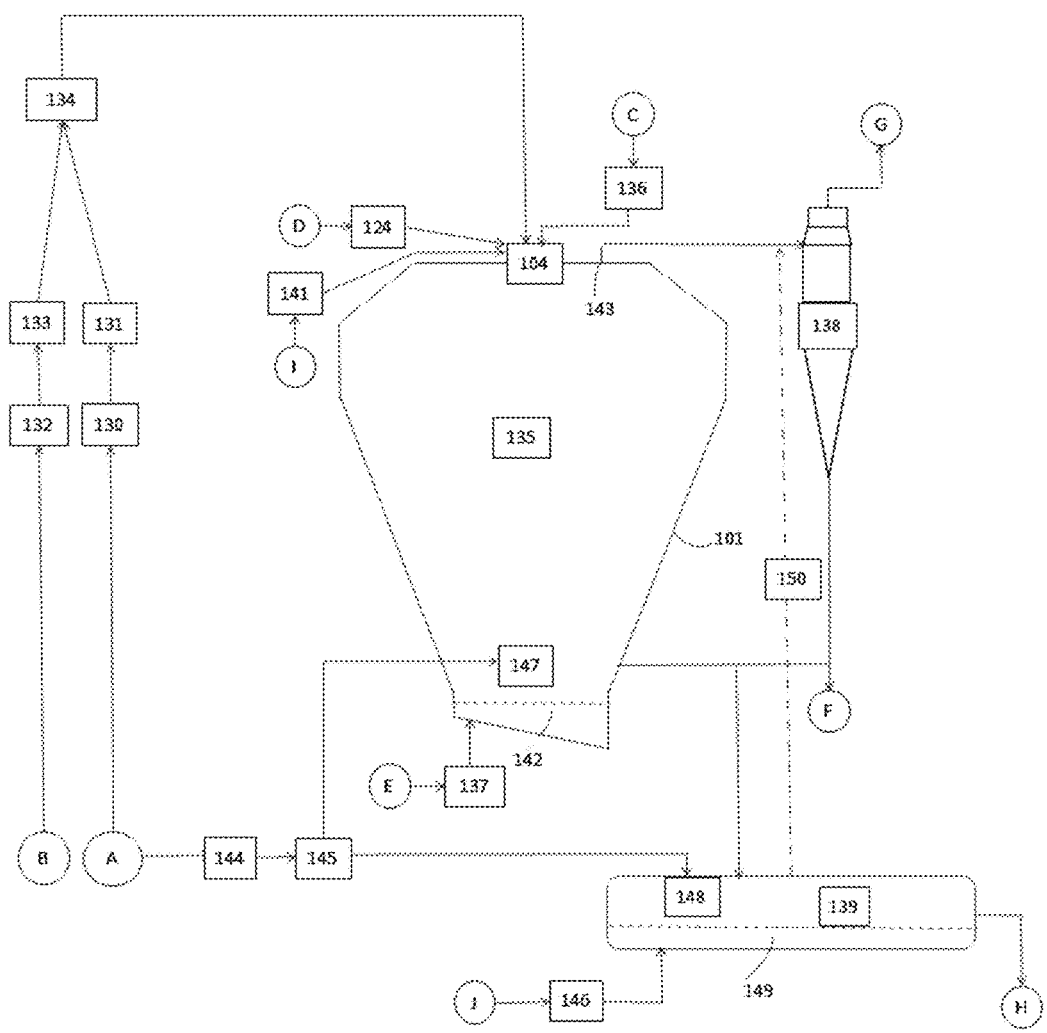

FIG. 6 is a diagram of the principle of a process according to the invention, carried out in a multiple effect tower and as described in FIG. 5, with A=A'=A".

Figure 7:
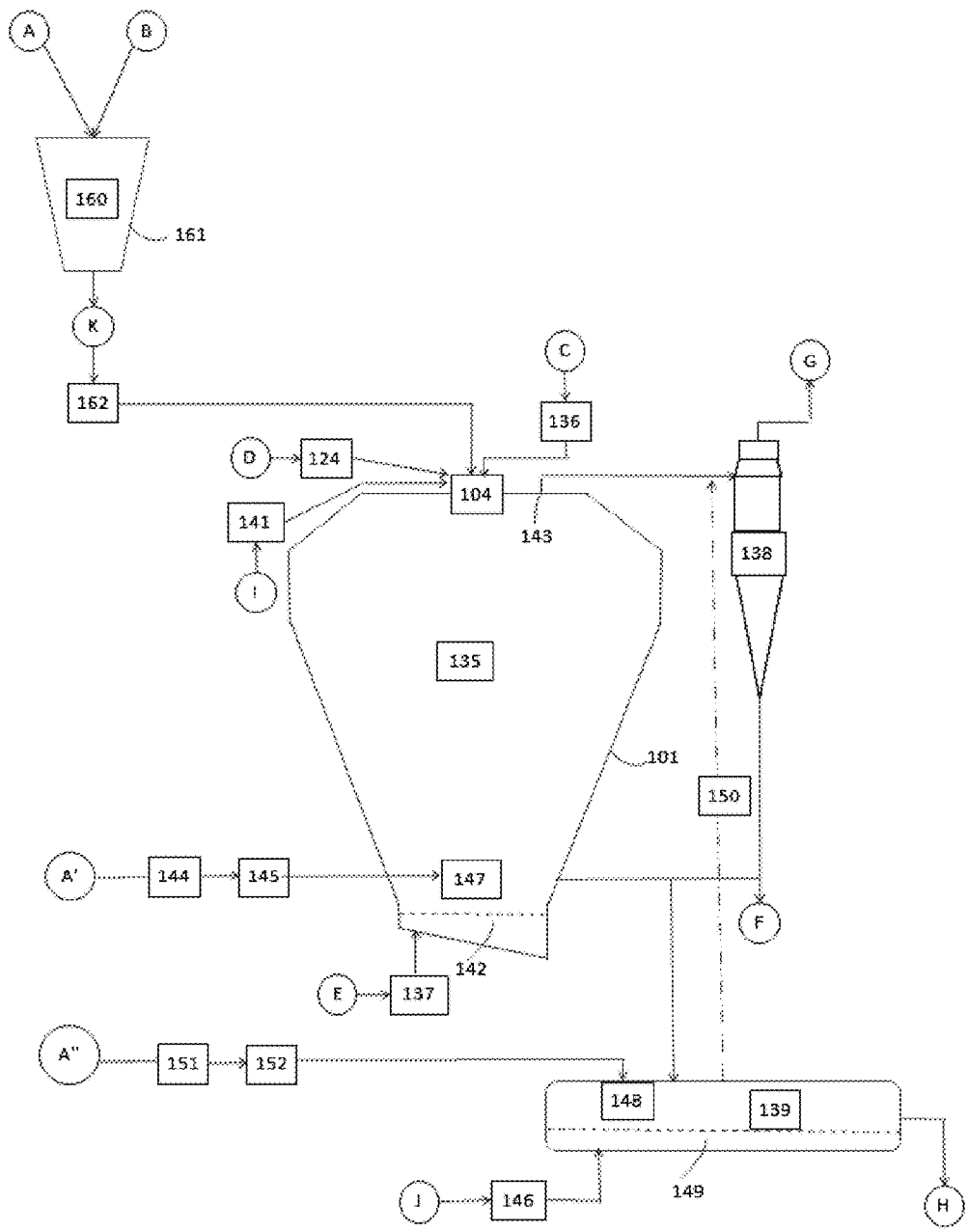

FIG. 7 is a diagram of the principle of a process according to the invention, carried out in a multiple effect tower.

An aqueous medium containing an acid, symbolized by the circle A is transferred into a reactor C equipped with a thermostatic jacket 161. An aqueous medium containing a metal or metal cation symbolized by the circle B is gradually added to the reactor C with stirring. The aqueous phase K resulting from the mixing between the aqueous medium A and the aqueous medium B, is fed, via the conveying pump 162 in order to be sprayed in the spray tower via the spraying device 104 intended for the production of monodisperse or polydisperse aerosols.

An aqueous medium containing an acid, symbolized by the circle A', optionally passes through a heater 144 and feeds, via a pump 145 the spraying device 147 intended for the production of aerosols.

An aqueous medium containing an acid, symbolized by the circle A", optionally passes through a heater 151 and feeds, via a pump 152 the spraying device 148 intended for the production of aerosols.

The circle C represents an additional device for spraying anti-agglomerating agent via a powder-metering device 136, if necessary.

The circle D represents the introduction of the hot vector gas, in particular air and/or inert gas, in the spray-drying version, via the fan 124.

The circle E represents the introduction of the secondary vector gas, for the drying and/or the final cooling of the stabilized final composition obtained, which is solid or undergoing solidification, via a fan 137.

The circle J represents the introduction of the vector gas onto the external vibrated fluidized bed 139, for the drying and/or the final cooling of the stabilized final composition obtained, which is solid or undergoing solidification via the fan 146.

A cyclone 138 separates all or some of the final product F that is to say the pulverulent composition, which is recovered, and the vector gas G which is discharged.

The external vibrated fluidized bed 139 allows the recovery of all or some of the final product H, that is to say the pulverulent composition, via the bottom of the tower.

The introduction of the secondary air E takes place through a permeable base 142 of the tower 135 in order to place the powder material in fluidized bed form. The spent air is discharged via an orifice 143 made through the upper wall of the chamber 101.

The introduction of the secondary air J takes place through a permeable base 149 of the vibrated fluidized bed 139 in order to place the powder material in fluidized bed form. The spent air is discharged via the line 150 connected to the inlet of the cyclone 138.

In this example, the spent air then passes through the cyclone 138 which produces, on the one hand, particles of product F and, on the other, air to be discharged G. Most of the particles are collected just above the permeable wall 142. FIG. 1 illustrates that the particles are collected either directly in F, or by means of the external fluidized bed 139 in H.

It is also possible to envision the addition, represented by the circle I, in the spray zone, of a powdered substance, in particular fine particles of the pulverulent composition that are recovered at the outlet of the cyclone 138, product F, or the installation, injected by means of the device 141 consisting mainly of a powder-metering device.

Figure 8:
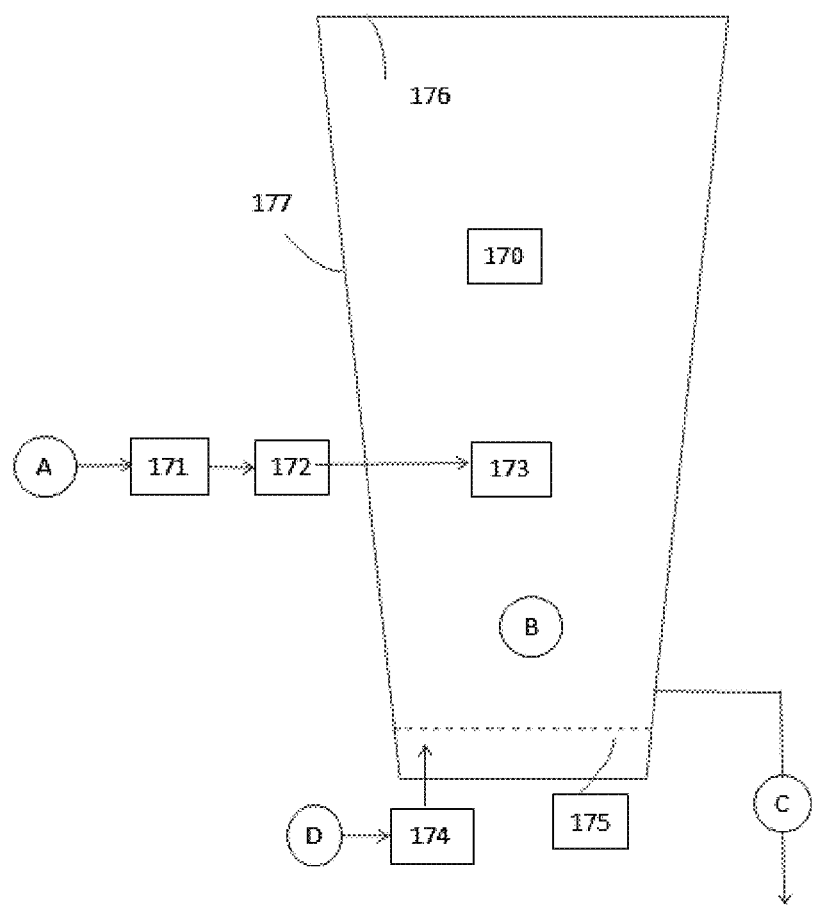

FIG. 8 is a diagram of the principle of a process according to the invention, carried out in a fluidized airbed.

A pulverulent composition of salt (HMTBA)$_2$Ca, symbolized by the circle B is incorporated into a fluidized airbed 170. An aqueous medium containing an acid, symbolized by the circle A, optionally passes through a heater 171 and feeds, via a pump 172 a spraying device 173 intended for the production of aerosols.

The circle D represents the introduction of the vector gas, for the drying and/or the final cooling of the stabilized final composition obtained, which is solid or undergoing solidification, via a fan 174.

The introduction of the gas D takes place through a permeable base 175 of the fluidized bed in order to place the powder matter B in fluidized bed form. The spent air is discharged through one or more filter(s) via an orifice 176 made through the upper wall of the chamber 177.

The final pulverulent composition H is recovered at the end of the batch during the emptying of the fluidized bed.

EXAMPLES

Examples 1 to 12 which follow illustrate the invention.

Example 1: Production of a Powder Having a TOS of 88.3% by Weight

One kilogram of salt (HMTBA)$_2$Ca at 85.5% of TOS, 11.7% of calcium and 2.3% moisture content was incorporated into a fluidized airbed having a working volume of 5 liters. 300 g of a solution of HMTBA at 88% of dry matter was sprayed onto this powder at a flow rate of 450 g/h, a spraying pressure of 1.5 bar and an input temperature on the fluidized airbed of 60° C. At the end of the spraying, the product was dried for 5 min.
The product obtained has a TOS of 88.3%, a calcium content of 9.2% and a moisture content of 1.3%. The mean particle size of this product is 191 µm, the bulk density is 390 g/L and the tapped density is 480 g/L.

Example 2: Production of a Powder Having a TOS of 89.3% by Weight

One kilogram of salt (HMTBA)$_2$Ca at 84.6% of TOS, 11.5% of calcium and 1.9% moisture content was incorporated into a fluidized airbed having a working volume of 5 liters. 504 g of a solution of HMTBA at 88% of dry matter were sprayed onto this powder at a flow rate of 250 g/H, a spraying pressure of 1.5 bar and an input temperature on the fluidized airbed of 60° C. At the end of the spraying, the product was dried for 5 min.
The product obtained has a TOS of 89.3%, a calcium content of 8% and a moisture content of 1.6%.

Example 3: Production of a Powder Having a 5.5TOS of 88.2% by Weight

Two kilograms of salt (HMTBA)$_2$Ca at 85.5% of TOS, 11.7% of calcium and 2.3% of moisture content were incorporated into a fluidized airbed having a working volume of 12 liters. 670 g of a solution of HMTBA at 88% of dry matter were sprayed onto this powder at a flow rate of 600 g/H, a spraying pressure of 1 bar and a fluidized airbed input temperature of 55° C. At the end of the spraying, the product was dried for 5 min.
The product obtained has a TOS of 88.2%, a calcium content of 8.8%, and a moisture content of 2.2%. The mean particle size of this product is 150 µm, the bulk density is 370 g/L, and the tapped density is 400 g/L.

Example 4: Production of a Powder Having a TOS of 88.1% by Weight

A milling step on a knife mill is carried out on two kilograms of a salt (HMTBA)$_2$Ca in the form of extruded material obtained according to patent FR2964968. The powder obtained post-milling has a TOS of 74%, a calcium content of 11.2%, a water content of 11% and a means particle size of 150 µm. One kilogram of this product is incorporated into a fluidized airbed having a working volume of 5 liters. 400 g of a solution of HMTBA at 88% of dry matter are then sprayed onto this powder at a flow rate of 300 g/H, a spraying pressure of 1.5 bar and a fluidized airbed input temperature of 60° C. The product is then dried for 30 min.
The product obtained has a TOS of 88.1%, a calcium content of 9.2%, and a moisture content of 1.4%. The mean particle size of this product is 250 µm and the bulk density is 510 g/L.

Example 5: Production of a Powder Having a TOS of 88.4% by Weight

One kilogram of salt (HMTBA)$_2$Ca at 85.5% of TOS, 11.7% of calcium and 2.3% of moisture content is incorporated into a fluidized airbed. 275 g of a solution of HMTBA at 95.47% of dry matter, heated to a temperature of 60° C. is sprayed onto this powder at a flow rate of 300 g/H, a spraying pressure of 1.5 bar and a fluidized airbed input temperature of 60° C. The product is then dried for 5 min.

The product obtained has a TOS of 88.4%, a calcium content of 8.9%, and a moisture content of 1.5%. The mean particle size of this product is 680 µm, the bulk density is 380 g/L, and the tapped density is 410 g/L.

Example 5a: Production of a Powder Having a TOS of 88.2% by Weight

Three kilograms of salt (HMTBA)$_2$Ca at 85.5% of TOS, 11.7% of calcium and 2.3% of moisture content are incorporated into a rotary granulator having a working volume of 5 liters of GLATT GRC3 type. 1 kg of a solution of HMTBA at 88% of dry matter is sprayed onto this powder at a flow rate 600 g/H, a spraying pressure of 1.5 bar, a granulator input temperature of 60° C. and disk rotation speed of 200 rom. The product is then dried for 5 min.
The product obtained has a TOS of 88.2%, a calcium content of 9.1% and a moisture content of 1.7%. The mean particle size of this product is 230 µm and the bulk density is 540 g/L.

Example 6: Production of a Powder Having a TOS of 88.1% by Weight

A powder of salt (HMTBA)$_2$Ca at 85.2% of TOS, 11.8% of calcium and 1.8% of moisture content was continuously fed into a multiple effect spray tower at a flow rate of 200 kg/H. A solution of HMTBA at 88% of dry matter was continuously sprayed in the bottom part of the spray tower. This solution was sprayed, on the one hand, onto the static bed of the industrial facility at a flow rate of 60 kg/h and a spraying pressure of 4 bar, and on the other hand, onto the vibro-fluidizer at a flow rate of 16 kg/H and a spraying pressure of 1.5 bar.
The temperature applied were 100° C. for the static bed temperature, 70° C. for the first part of the vibro-fluidizer and 30° C. for the second part of the vibro-fluidizer.
The product obtained has a TOS of 88.1%, a calcium content of 9.1%, and a moisture content of 1.4%. The mean particle size of this product is 196 µm, the bulk density is 530 g/L and the tapped density at 10 taps is 560 g/L.

Example 7: Production of a Powder Having a TOS of 88.5% by Weight

A powder of salt (HMTBA)$_2$Ca at 85.18% of TOS, 11.78% of calcium and 1.79% of moisture content is continuously fed into a multiple effect tower at a flow rate of 200 kg/H. A solution of HMTBA at 96% of dry matter, heated to a temperature of 60° C. so as to lower its viscosity below 200 centipoises, is continuously sprayed in the bottom part of the drying tower. This solution is sprayed, on the one hand, onto the static bed of the industrial installation at a flow rate of 48 kg/h and a spraying pressure of 3.5 bar, and on the other hand, onto the vibro-fluidizer at a flow rate of 13 kg/H and a spraying pressure of 1.5 bar.
The temperatures of the liquid feed lines are thermostated at 60° C. so as to ensure satisfactory spraying of the concentrated HMTBA solution.
The temperatures applied are 100° C. for the static bed temperature, 70° C. for the first part of the vibro-fluidizer and 30° C. for the second part of the vibro-fluidizer.
The product obtained has a TOS of 88.5%, a calcium content of 8.8%, and a moisture content of 1.3%. The mean particle size of this product is 250 µm and the bulk density is 550 g/L.

Example 8: Production of a Powder Having a TOS of 88.3% by Weight

A lime milk produced at 30% of dry matter and a solution of HMTBA at 88% of dry matter are continuously mixed according to the conditions of patent FR2988091.
The feed flow rates are respectively 95 kg/H for the lime milk and 130 kg/H for the HMTBA solution.
The reaction mixture is sprayed by means of a nozzle according to the knowledge of those skilled in the art, in a multiple effect spray tower with an input temperature of 180° C. and an output temperature of 102° C.
At the bottom of the tower, a solution of HMTBA at 88% of EST is sprayed, on the one hand, onto the static bed of the MSD tower at a flow rate of 35 kg/h and a spraying pressure of 3 bar, and on the other hand, onto the vibro-fluidizer at a flow rate of 10 kg/H and a spraying pressure of 1.5 bar.
The temperatures applied are 70° C. for the static bed temperature, 60° C. for the first part of the vibro-fluidizer and 30° C. for the second part of the vibro-fluidizer.
The product obtained has a TOS of 88.3%, a calcium content of 8.9%, and a moisture content of 1.6%. The mean particle size of this product is 180 µm and the bulk density is 420 g/L.

Example 9: Production of a Powder Having a TOS of 88.6% by Weight

A lime milk produced at 30% of dry matter and a solution of HMTBA at 88% of dry matter are continuously mixed in an atomization turbine (of NIRO Atomizer type). The feed flow rates were respectively 3.5 kg/H for the lime milk and 4.5 kg/H for the HMTBA solution.
The reaction mixture was atomized in a single effect spray tower at an input temperature of 140° C. and an output temperature of 85° C.
The product was then taken up in a fluidized airbed in order to simulate a multiple effect tower.
330 g of a solution of HMTBA at 88% of dry matter were sprayed onto 1 kg of previously produced powder at a flow rate of 300 g/H, a spraying pressure of 1.5 bar and a fluidized airbed input temperature of 60° C. At the end of the spraying, the product was dried for 5 min.
The product obtained has a TOS of 88.6%, a calcium content of 8.7% and a moisture content of 1.5%.

Example 10: Production of a Powder Having a TOS of 88.6% by Weight

A lime milk produced at 37% of dry matter and a solution of HMTBA at 88% of dry matter are continuously mixed according to the conditions of patent FR2988091.
The feed flow rates are respectively 90 kg/H for the lime milk and 150 kg/H for the HMTBA solution.
The mixture is sprayed by means of a nozzle according to the knowledge of those skilled in the art in a multiple effect spray tower with an input temperature of 180° C. and an output temperature of 105° C.
At the bottom of the tower, a concentrated solution of HMTBA at 96% of dry matter is sprayed, on the one hand, onto the static bed of the MSD tower at a flow rate of 31 kg/h and a spraying pressure of 3 bar, and on the other hand, onto the vibro-fluidizer at a flow rate of 16 kg/H and a spraying pressure of 1.5 bar.
The temperatures of the liquid feed lines are thermostated at 60° C.
The temperatures applied are 70° C. for the static bed temperature, 60° C. for the first part of the vibro-fluidizer and 30° C. for the second part of the vibro-fluidizer.

The product obtained has a TOS of 88.6%, a calcium content of 8.7%, and a moisture content of 1.3%. The mean particle size of this product is 210 μm and the bulk density is 430 g/L.

Example 11: Production of a Powder Having a TOS of 88.2% by Weight

A lime milk produced at 30% of dry matter and a solution of HMTBA at 88% of dry matter are continuously mixed according to the conditions of patent FR2988091.
The feed flow rates are respectively 75 kg/H for the lime milk and 102 kg/H for the HMTBA solution.
The reaction mixture is sprayed by means of a nozzle according to the knowledge of those skilled in the art, in a multiple effect spray tower with an input temperature of 160° C. and an output temperature of 85° C. The drying is carried out under nitrogen in a tower equipped with a closed-circuit gas recycling system.
At the bottom of the tower, a solution of HMTBA at 88% of EST is sprayed, on the one hand, onto the static bed of the MSD at a flow rate of 20 kg/h and a spraying pressure of 3 bar, and on the other hand, onto the vibro-fluidizer at a flow rate of 15 kg/H and a spraying pressure of 1.5 bar.
The temperatures applied are 60° C. for the static bed temperature, 50° C. for the first part of the vibro-fluidizer and 20° C. for the second part of the vibro-fluidizer.
The product obtained has a TOS of 88.2%, a calcium content of 9%, and a moisture content of 1%. The mean particle size of this product is 240 μm and the bulk density is 480 g/L.

Example 12

Production of a Powder Comprising HMTBA According to A process not Belonging to the Present Invention, and Comparison of the Product Obtained with the Product According to the Invention.

The production is carried out batchwise in a Z-arm mixer open to the atmosphere.
372 g of a crystalline $HMTBA_2(Ca)$ powder were incorporated into the mixer and then heated to 85° C. by means of the jacket of the equipment.
A solution of HMTBA at 88% of dry matter was added four times, and at intervals of 15 min, to the operating mixer. The amounts added were 93 g, 92 g, 94 g and 96 g. At the end of the final addition, the preparation was kept stirring for 37 min at a temperature of 73-82° C. The paste recovered then underwent a drying operation for 24 h in the oven at 70° C.
The product obtained post-drying was then milled so as to obtain coarse particles.
A comparative analysis of the products produced according to example 12 and according to example 1 of the present application was carried out.
The table below indicates the physical and chemical properties of powders.

|  | Example 1 (Process belonging to the present invention) | Example 12 (Process not belonging to the present invention) |
|---|---|---|
| Physical properties | | |
| Particle size, μm | Product with homogeneous particle size Gaussian Curve with a median at approximately 200 μm | Product with heterogeneous particle size with agglomerates which are a few mm to several tens of cm |
| Bulk density, g/l | 370 | 680 |
| Chemical properties | | |
| Moisture content, % | 1.5 | 1 |
| Calcium, % | 10.1 | 9.4 |
| TOS, % | 88.4 | 89.9 |

Figure 2:
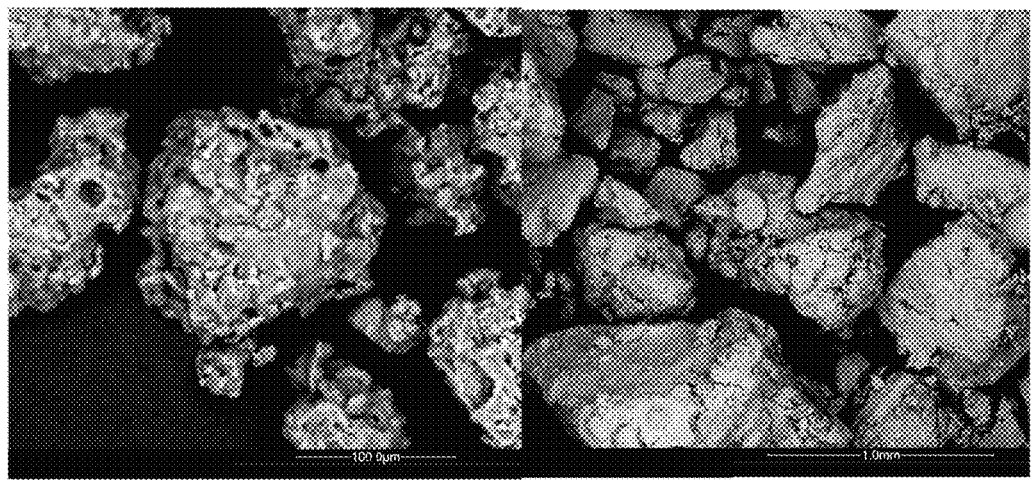
FIG. 2A is a scanning optical microscopy image relating to the powder obtained at the end of example 1.
FIG. 2B is a scanning optical microscopy image relating to the powder obtained at the end of example 12.
Figure 3A:
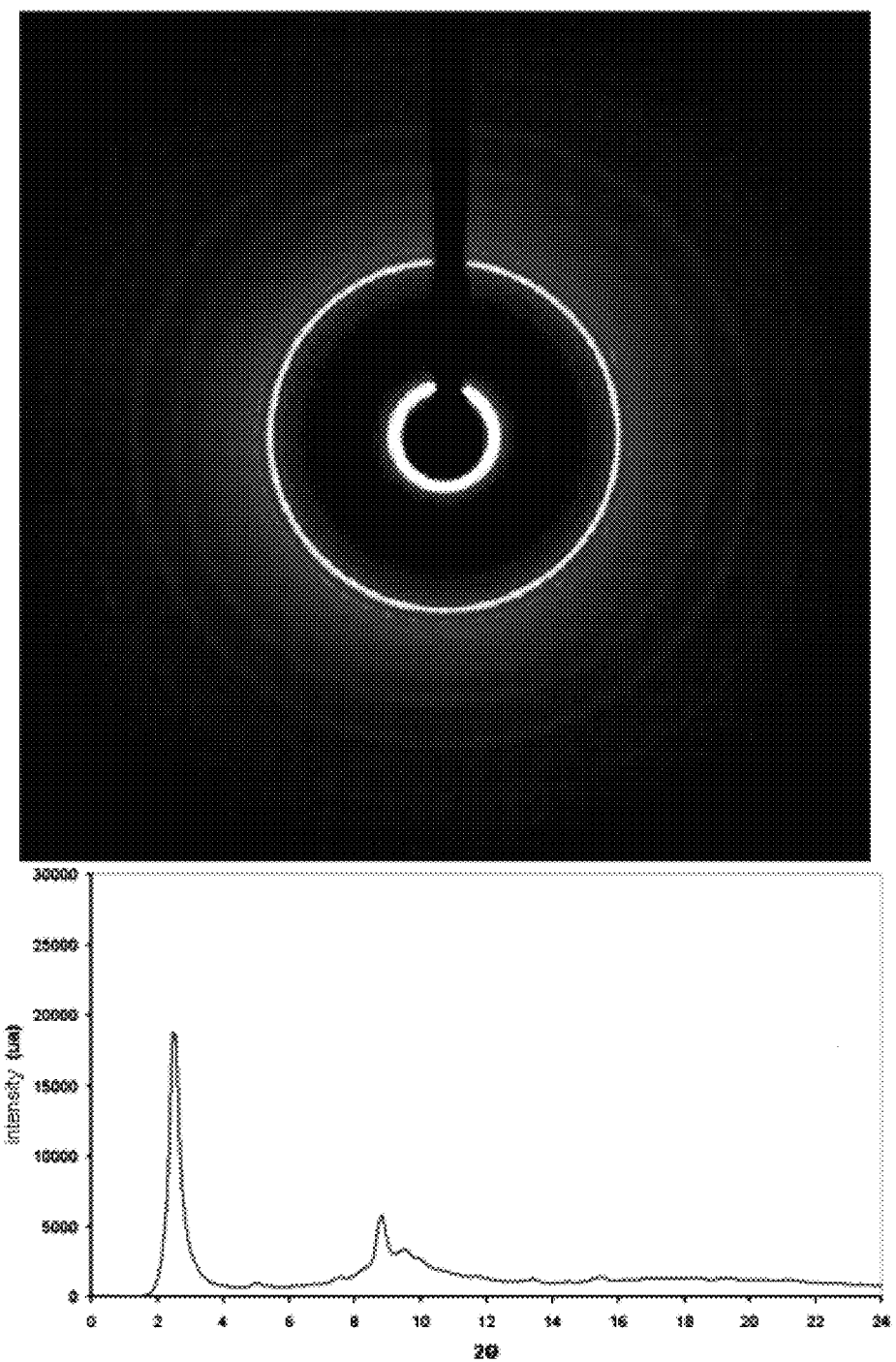
FIG. 3A shows the X-ray analysis spectrum of powders of sample A between $2\theta=1°$ and $2\theta=24°$ obtained using a radiation Mo—K$\alpha$ ($\lambda$=0.71073 Å).
Figure 3B:
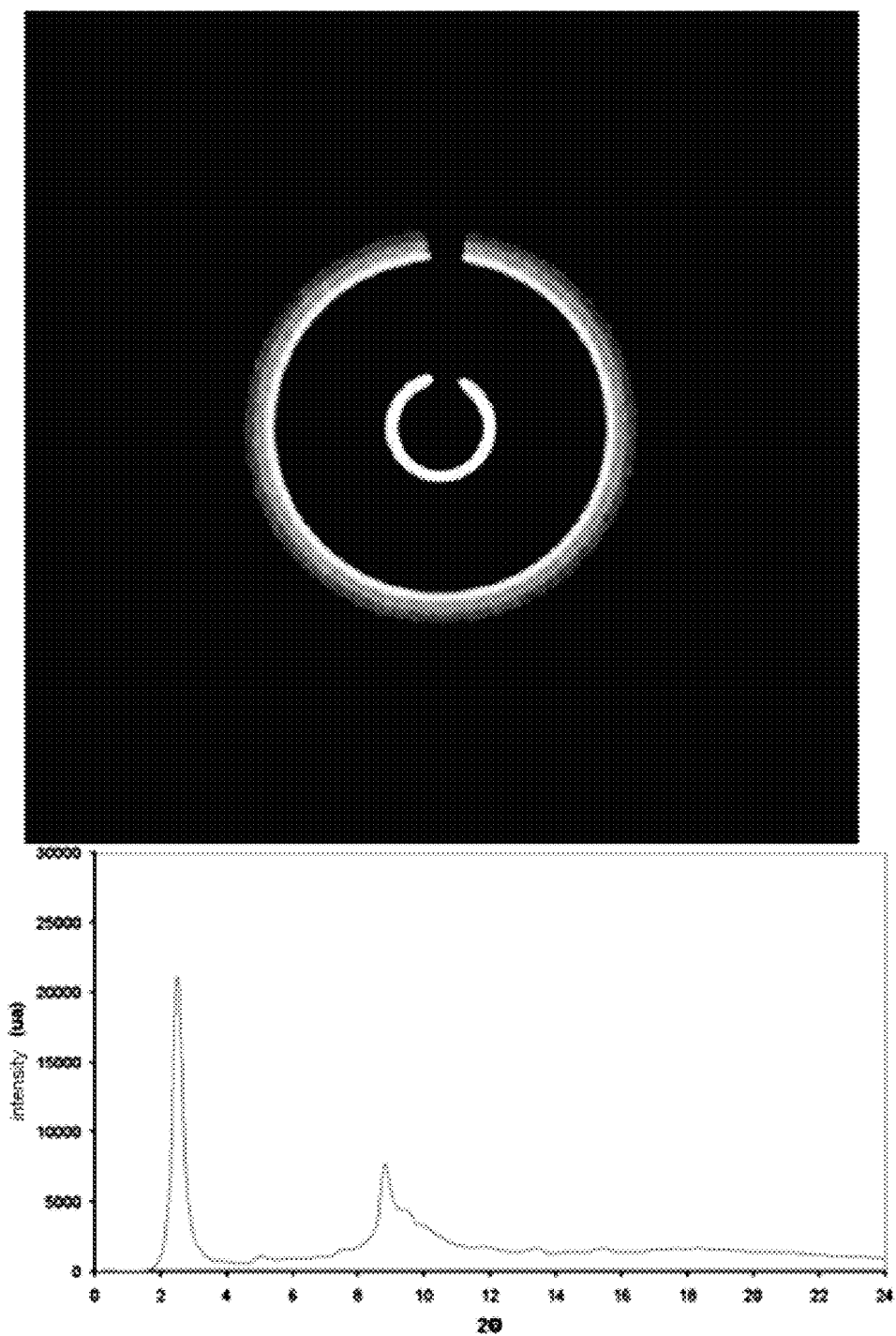
FIG. 3B shows the X-ray analysis spectrum of powders of sample B between $2\theta=1°$ and $2\theta=24°$ obtained using a radiation Mo—K$\alpha$ ($\lambda$=0.71073 Å).
Figure 3C:
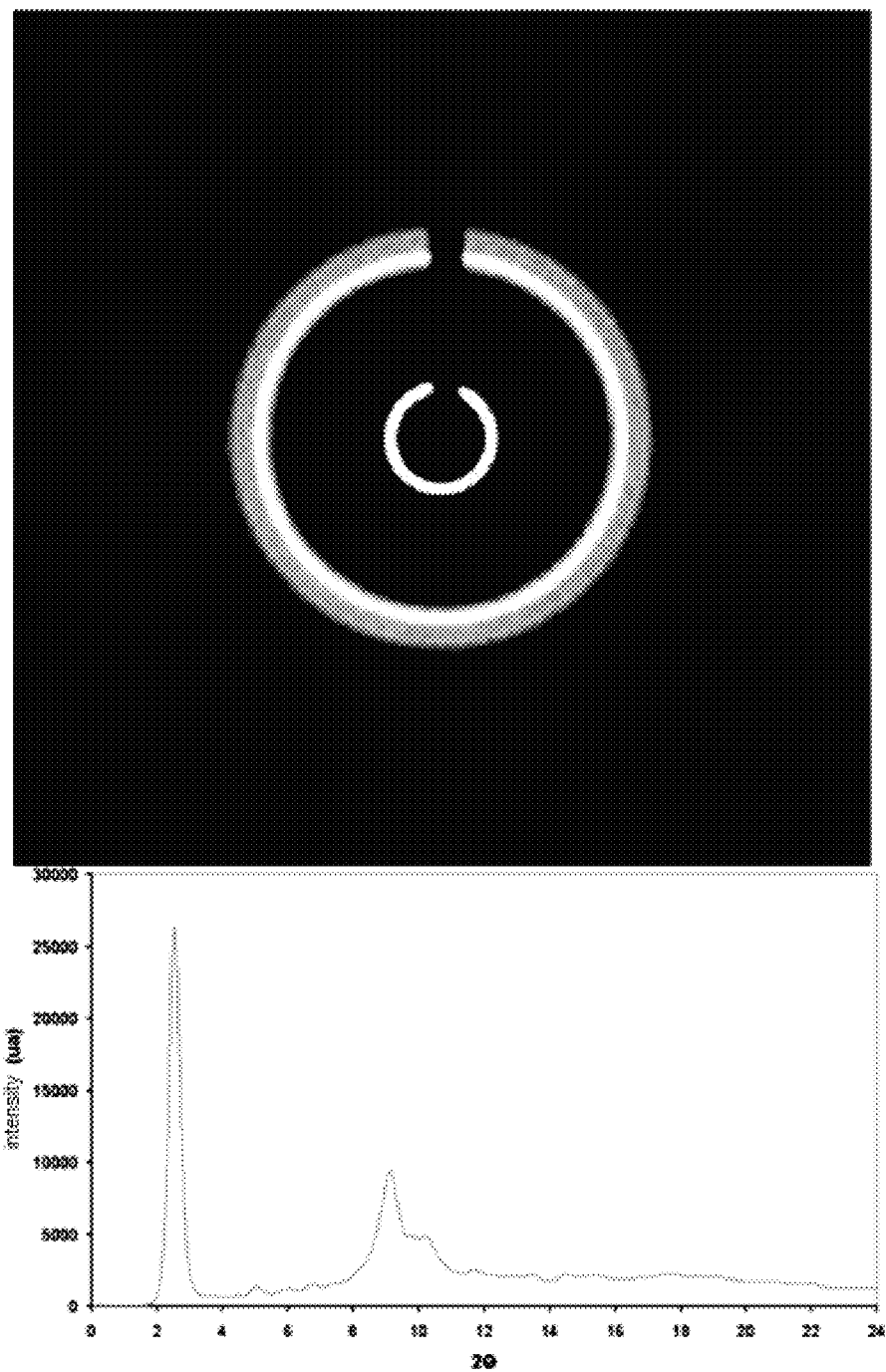
FIG. 3C shows the X-ray analysis spectrum of powders of sample C between $2\theta=1°$ and $2\theta=24°$ obtained using a radiation Mo—K$\alpha$ ($\lambda$=0.71073 Å).

These results very clearly indicate a significant difference with regard to the physical properties of these powders. Example 12 results in the obtaining of granules that are heterogeneous in size with a density >650 g/l, whereas example 1 of the present application results in the obtaining of a powder that is homogeneous in size with a density close to 400 g/l.
Other analyses make it possible to distinguish the two types of products. Thus, the visual appearance of the powders was studied under an optical microscope (FIG. 1) and under a scanning optical microscope (FIG. 2).
The particles produced according to example 1 are small spherical particles, with quite a narrow particle size distribution, and cream in color.
The particles of example 12 are compact aggregates which may be angular, heterogeneous in size and shape, brown in color and with a smooth surface appearance.
The X-ray analysis also made it possible to demonstrate differences with regard to the degree of crystallinity of the particles obtained according to the process (FIG. 3), linked to the intensity of the peak at 2theta=9°.
These results make it possible to propose a classification in increasing order of crystallinity

A<B<C.

Sample A corresponds to the powder of salt of formula (I) $(HMTBA)_2Ca$ obtained in example 9, before spraying: it is the core of salt of formula (I) $(HMTBA)_2Ca$, without exterior layer.
Sample B corresponds to the powder obtained at the end of example 1.
Sample C corresponds to the powder obtained at the end of example 12.
Powder A (core of salt of formula (I) without exterior layer) and powder B (subject of the present invention), are thus less crystalline than powder C.

Example 13: SEM Analysis Coupled to X-Ray Emission Spectrometry of the Particles Obtained According to Example 3

An SEM analysis coupled to X-ray emission spectrometry was carried out on a particle produced according to example 3 in such a way as to demonstrate the difference in chemical composition between the core and the exterior of the particle (FIG. 4). The interior quantification (FIG. 4A) is the following:

| Element | % Weight | % At |
|---|---|---|
| C | 44.11 | 62.47 |
| O | 17.88 | 19.01 |
| S | 22.58 | 11.98 |
| Ca | 15.42 | 6.54 |
| Total | 100.00 | 100.00 |

The S/Ca atomic ratio is, in the interior of the particle (in the core), approximately 1.8.

The exterior quantification (FIG. 4B) is the following:

| Element | % Weight | % At |
|---|---|---|
| C | 53.01 | 67.39 |
| O | 22.74 | 21.70 |
| S | 17.60 | 8.38 |
| Ca | 6.65 | 2.53 |
| Total | 100.00 | 100.00 |

The S/Ca atomic ratio is, on the exterior of the particle (at its surface), approximately 3.3. This analysis makes it possible to demonstrate a difference in chemical composition between the core of the particle and the exterior of the particle, in particular with regard to the calcium percentage. The theoretical chemical composition of the salt of formula (I) (HMTBA)$_2$Ca and of the complex of formula (II) (HMTBA)$_4$Ca is the following:

Form salt of formula (I)=338 g/mol

| Atoms | Numbers | Total molecular weight, g/mol | % relative to molecular weight of the molecule in question |
|---|---|---|---|
| Carbon | 10 | 120 | 35.5 |
| Oxygen | 6 | 96 | 28.4 |
| Sulfur | 2 | 64 | 18.9 |
| Hydrogen | 18 | 18 | 5.32 |
| Calcium | 1 | 40 | 11.8 |

The S/Ca theoretical atomic ratio is, for the salt of formula (I), approximately 1.6.

Form complex of formula (II)=636 g/mol

| Atoms | Numbers | Total molecular weight, g/mol | % relative to molecular weight of the molecule in question |
|---|---|---|---|
| Carbon | 20 | 240 | 37.7 |
| Oxygen | 12 | 192 | 30.1 |
| Sulfur | 4 | 128 | 20.1 |
| Hydrogen | 36 | 36 | 5.6 |
| Calcium | 1 | 40 | 6.28 |

The S/Ca theoretical atomic ratio is, for the salt of formula (I), approximately 3.2.

The comparison between the theoretical values and the measured values with regard to the % of sulfur and the calcium indicates the presence of a salt of formula (I) of HMBTA on the inside of the particle and of a complex of formula (II) on the outside.

The invention claimed is:

1. A particle comprising:
a core consisting essentially of a salt of formula (I) below:

$$(A^-)_n M^{n+} \quad (I)$$

in which:
A$^-$ represents an anion chosen from the group consisting of 2-hydroxy-4-methylthiobutanoate, methioniate and cysteinate,
M represents a divalent or trivalent metal,
n being equal to 2 when said metal is divalent and to 3 when said metal is trivalent, and
a layer comprising a compound B chosen from the group consisting of 2-hydroxy-4-methylthiobutanoic acid (HMTBA), methionine, cysteine, mixtures thereof, salts thereof and complexes thereof,
said layer coating said core,
the weight percentage of said compound B relative to the salt of formula (I) of the core being from approximately 10% to approximately 50%,
said compound B not being, or not only being, in the form of a salt of formula (I),
the organosulfur compound content (TOS) of said particle being greater than 87% by weight relative to the total weight of said particle.

2. A particle according to claim 1, wherein said compound B is in the:
free form, chosen from 2-hydroxy-4-methylthiobutanoic acid (HMTBA), methionine and cysteine, and/or
form of salt of said formula (I), and/or
form of a complex of formula (A)$_4$M (II) in which A and M are as defined,
said compound B not being, or not only being, in the form of a salt of formula (I),
said compound B being in the:
free form,
form of the complex of formula (II),
form of a mixture of the free form and of the complex of formula (II),
form of a mixture of the free form and of the salt of formula (I),
form of a mixture of the salt of formula (I) and of the complex of formula (II), or
form of a mixture of the free form, of the salt of formula (I) and of the complex of formula (II).

3. A particle according to claim 1, wherein:
the water content is less than 3% by weight of the particle,
the calcium content is from 6% to 11% by weight of the particle, or
the weight percentage of said compound B relative to the salt of formula (I) of the core is from approximately 10% to approximately 40%.

4. A particle according to claim 1 wherein said metal is selected from the group consisting of Mg, Be, Ca, Sr, Ba, Mn, Fe, Co, Ni, Cu, Zn, Pt, B, Al, Ga, and In, and said salt of formula (I) is selected from the group consisting of (HMTBA)$_2$Ca, (HMTBA)$_2$Mg, (HMTBA)$_2$Fe, (HMTBA)$_2$Mn, (HMTBA)$_2$Zn, (HMTBA)$_2$Cu, (HMTBA)$_3$Fe, (HMTBA)$_3$Al, (Methionine)$_2$Ca, (Methionine)$_2$Mg, (Methionine)$_2$Fe, (Methionine)$_2$Mn, (Methionine)$_2$Zn, (Methionine)$_2$Cu, (Methionine)$_3$Fe, (Methionine)$_3$Al, (Cysteine)$_2$Ca, (Cysteine)$_2$Mg, (Cysteine)$_2$Fe, (Cysteine)$_2$Mn, (Cysteine)$_2$Zn, (Cysteine)$_2$Cu, (Cysteine)$_3$Fe, and (Cysteine)$_3$Al.

5. A particle according to claim 1, wherein:
said anion A$^-$ is 2-hydroxy-4-methylthiobutanoate, and/or
said compound B included in said layer is 2-hydroxy-4-methylthiobutanoic acid (HMTBA), or a salt or complex thereof.

6. A pulverulent composition consisting of or comprising particles according to claim 1.

7. A pulverulent composition of particles according to claim 6, wherein the particle size of said particles ranges from 10 to 3000 μm [Dv(0,5)].

8. A pulverulent composition according to claim 6, in which:
the bulk density is greater than 350 g/L,
or
the tapped density is greater than 400 g/L.

9. A pulverulent composition according to claim 6, comprising oil in addition to said particles.

10. A process for producing a particle comprising:
a core consisting essentially of a salt of formula (I) below:

$$(A^-)_n M^{n+} \quad (I)$$

in which:
A⁻ represents an anion chosen from the group consisting of 2-hydroxy-4-methylthiobutanoate, methioniate and cysteinate,
M represents a divalent or trivalent metal,
n being equal to 2 when said metal is divalent and to 3 when said metal is trivalent, and
a layer comprising a compound B chosen from the group consisting of 2-hydroxy-4-methylthiobutanoic acid (HMTBA), methionine and cysteine,
said layer coating said core,
the weight percentage of said compound B relative to the salt of formula (I) of the core being from approximately 10% to approximately 50%,
said compound B not being, or not only being, in the form of a salt of formula (I),
the organosulfur compound content (TOS) of said particle being greater than 87% by weight relative to the total weight of said particle,
said process comprising a step of spraying, onto a solid consisting essentially of a salt of formula (I) as defined above, a composition comprising a compound B chosen from the group consisting of 2-hydroxy-4-methylthiobutanoic acid (HMTBA), methionine and cysteine, the weight of said compound B being from approximately 10% to approximately 50% of the weight of the salt of formula (I) of the solid,
in order to obtain said particle.

11. A process according to claim 10, wherein said spraying step is carried out:
batchwise or continuously in a fluidized airbed,
or
on a vibro-fluidizer,
or
in a spray tower by co-spraying.

12. A process according to claim 10, wherein the core consisting essentially of a salt of formula (I) is obtained:
by reactive atomization,
in a fluidized airbed, in a granulator, in a rotary granulator, or in a mixer,
by a reactive extrusion, or
by means of a static or dynamic mixer.

13. The particle of claim 4, wherein the salt of formula (I) is a salt of formula (HMTBA)₂Ca, (HMTBA)₂Mg, (HMTBA)₂Fe, (HMTBA)₂Mn, (HMTBA)₂Zn, (HMTBA)₂Cu, (Methionine)₂Ca, (Methionine)₂Mg, (Methionine)₂Fe, (Methionine)₂Mn, (Methionine)₂Zn, (Methionine)₂Cu, (Cysteine)₂Ca, (Cysteine)₂Mg, (Cysteine)₂Fe, (Cysteine)₂Mn, (Cysteine)₂Zn or (Cysteine)₂Cu.

14. The particle of claim 2, wherein A represents 2-hydroxy-4-methylthiobutanoic acid (HMTBA).

15. The particle of claim 3, wherein the calcium content is from 6.5% to 10% by weight of the particle.

16. The particle of claim 3, wherein the calcium content is from 7% to 9% by weight of the particle.

17. The particle of claim 3, wherein the calcium content is approximately 8% by weight of the particle.

18. The particle of claim 3, wherein the weight percentage of said compound B relative to the salt of formula (I) of the core is from approximately 15% to approximately 35%.

19. The particle of claim 3, wherein the weight percentage of said compound B relative to the salt of formula (I) of the core is from approximately 20% to approximately 32%.

20. A particle according to claim 2, wherein said metal is selected from the group consisting of Mg, Be, Ca, Sr, Ba, Mn, Fe, Co, Ni, Cu, Zn, Pt, B, Al, Ga, and In and said salt of formula (I) is selected from the group consisting of (HMTBA)₂Ca, (HMTBA)₂Mg, (HMTBA)₂Fe, (HMTBA)₂Mn, (HMTBA)₂Zn, (HMTBA)₂Cu, (HMTBA)₃Fe, (HMTBA)₃Al, (Methionine)₂Ca, (Methionine)₂Mg, (Methionine)₂Fe, (Methionine)₂Mn, (Methionine)₂Zn, (Methionine)₂Cu, (Methionine)₃Fe, (Methionine)₃Al, (Cysteine)₂Ca, (Cysteine)₂Mg, (Cysteine)₂Fe, (Cysteine)₂Mn, (Cysteine)₂Zn, (Cysteine)₂Cu, (Cysteine)₃Fe, and (Cysteine)₃Al.

* * * * *